United States Patent [19]
Feith et al.

[11] Patent Number: 6,152,913
[45] Date of Patent: *Nov. 28, 2000

[54] MEDICAL LUER CONNECTION HAVING PROTECTIVE CAP WITH CRUSH RIB

[75] Inventors: Raymond P. Feith, Rialto; Gary S. Werschmidt, Yorba Linda; Tim Truitt, Orange, all of Calif.

[73] Assignee: The KippGroup, Ontario, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/834,090

[22] Filed: Apr. 14, 1997

Related U.S. Application Data

[63] Continuation-in-part of application No. 08/431,073, Apr. 27, 1995, Pat. No. 5,620,427.

[51] Int. Cl.[7] .................................. A61M 25/16
[52] U.S. Cl. ........................................ 604/533
[58] Field of Search .................. 215/320, 330, 215/331, 343, 344; 604/523, 533, 535, 538

[56] References Cited

U.S. PATENT DOCUMENTS

| | | | |
|---|---|---|---|
| 4,125,201 | 11/1978 | Birch | 215/330 |
| 4,296,949 | 10/1981 | Muetterties et al. | |
| 4,310,101 | 1/1982 | Sekine | 215/331 X |
| 4,325,487 | 4/1982 | Libit | 215/330 |
| 4,346,703 | 8/1982 | Dennehey et al. | |
| 4,349,116 | 9/1982 | Luenser | 215/330 |
| 4,439,188 | 3/1984 | Dennehey et al. | |
| 4,452,473 | 6/1984 | Ruschke | 604/241 |
| 4,461,394 | 7/1984 | Sendel et al. | 315/330 |
| 4,607,868 | 8/1986 | Dennehey et al. | |
| 4,629,455 | 12/1986 | Kanno | 604/241 |
| 4,697,715 | 10/1987 | Beruvides | 215/330 |
| 4,770,308 | 9/1988 | Lynn | 215/330 |
| 4,778,447 | 10/1988 | Velde et al. | |
| 4,880,414 | 11/1989 | Whipple | |
| 4,963,133 | 10/1990 | Whipple | |
| 4,991,413 | 2/1991 | Arnaldo | |
| 4,991,629 | 2/1991 | Ernesto et al. | |
| 5,125,915 | 6/1992 | Berry et al. | |
| 5,213,224 | 5/1993 | Luch | 220/296 X |
| 5,215,538 | 6/1993 | Larkin | |
| 5,224,515 | 7/1993 | Foster et al. | |
| 5,267,966 | 12/1993 | Paul | |
| 5,292,020 | 3/1994 | Narin | 215/331 X |
| 5,398,530 | 3/1995 | Derman | |
| 5,439,452 | 8/1995 | McCarty | |
| 5,442,941 | 8/1995 | Kahonen et al. | |
| 5,456,676 | 10/1995 | Nelson et al. | |
| 5,462,186 | 10/1995 | Ladina et al. | 215/330 |
| 5,690,241 | 11/1997 | Montgomery | 215/330 X |
| 5,782,808 | 7/1998 | Folden | 604/265 |
| 5,792,120 | 8/1998 | Menyhay | 604/256 |

FOREIGN PATENT DOCUMENTS

| | | | |
|---|---|---|---|
| 1509625 | 1/1968 | France | 215/331 |
| 1804099 | 7/1969 | Germany | 215/331 |

*Primary Examiner*—Sharon Kennedy
*Attorney, Agent, or Firm*—Richard L. Myers

[57] ABSTRACT

A protective cap for use with a luer lock system. The protective cap includes a tubular body having an inner surface and a closed end. Internal threads are formed on the inner surface which are sized and shaped to engage with an external threads on the associated luer component. A crush thread is formed adjacent to a portion of the inner threads and protrudes radially inward from the inner surface of the protective cap. The crush thread is configured for engagement with the external threads on the luer component such that when the protective cap is threaded onto the luer component, the crush threads frictionally interfere with the external threads. This frictional interference resists decoupling and thus removal of the protective cap from the luer component.

24 Claims, 14 Drawing Sheets

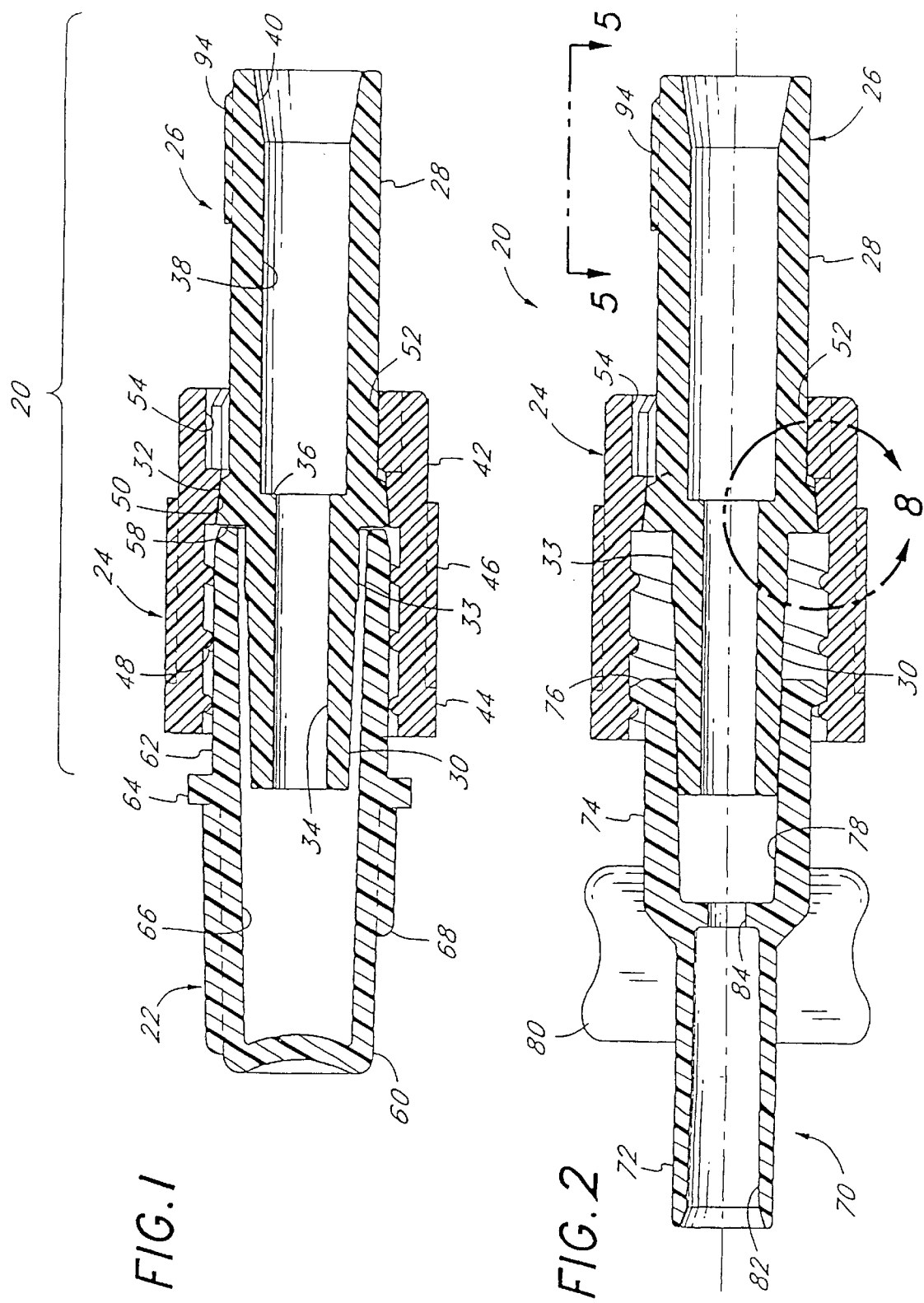

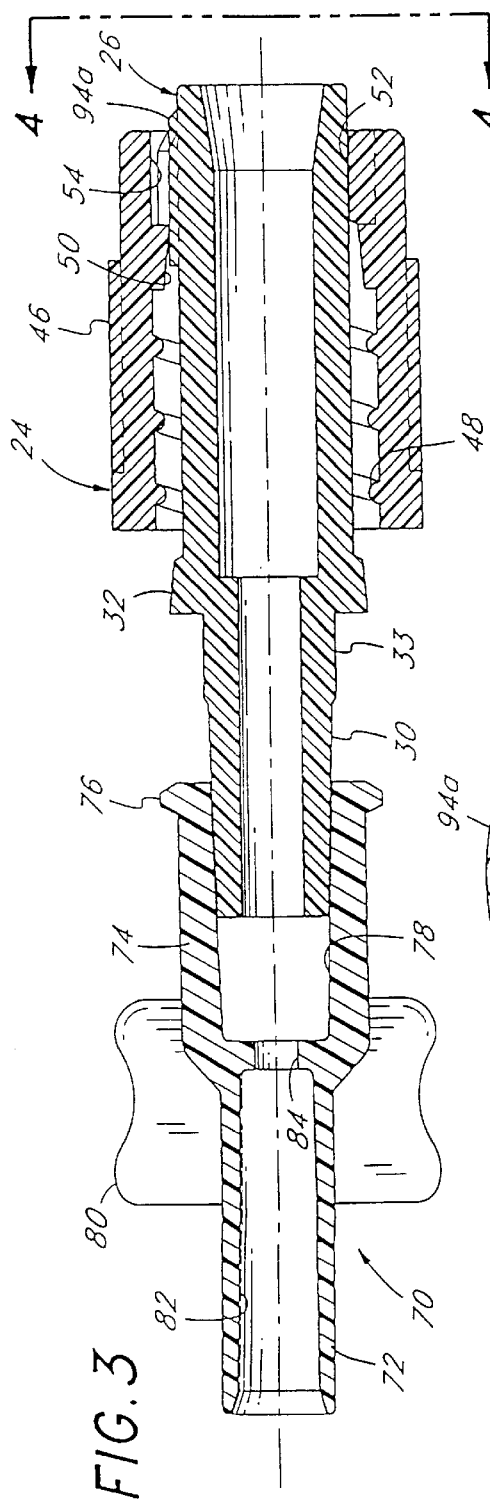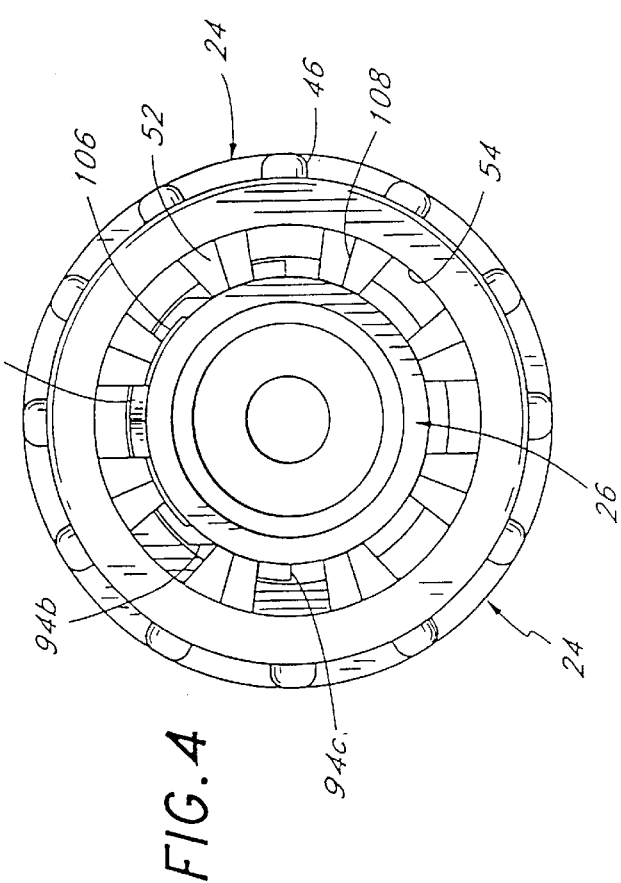

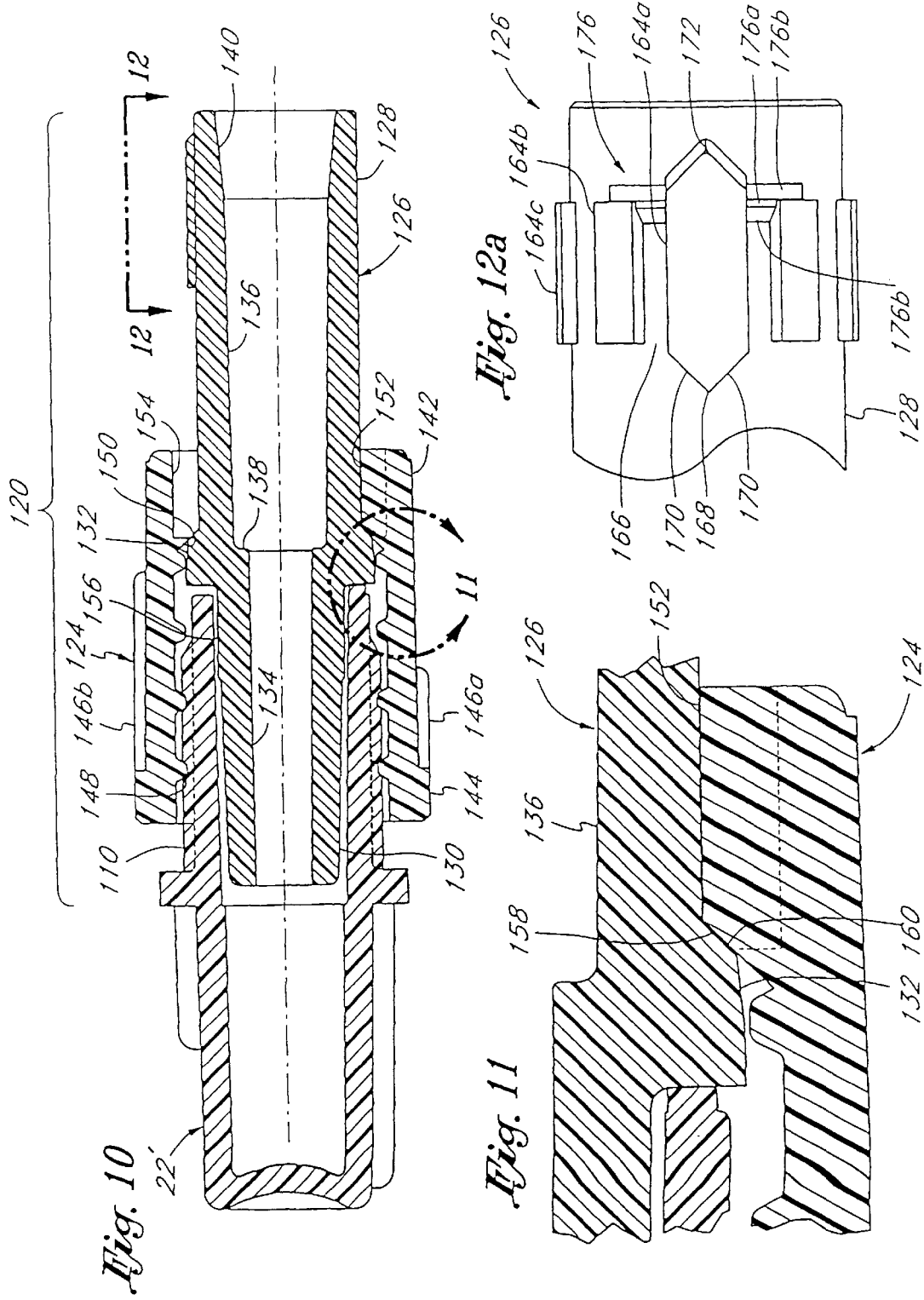

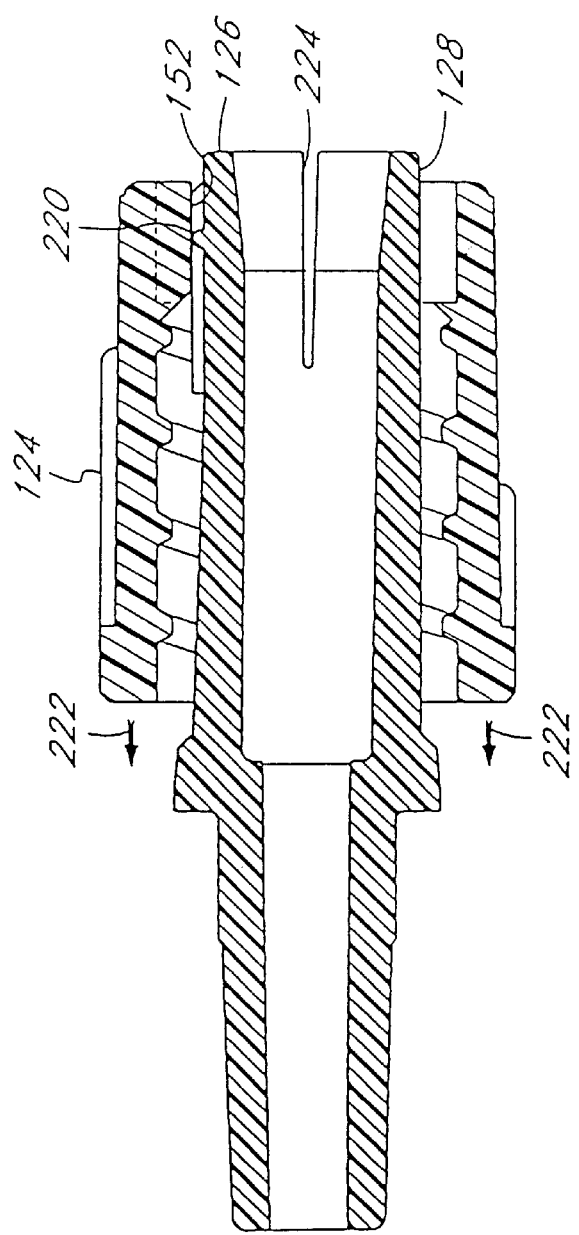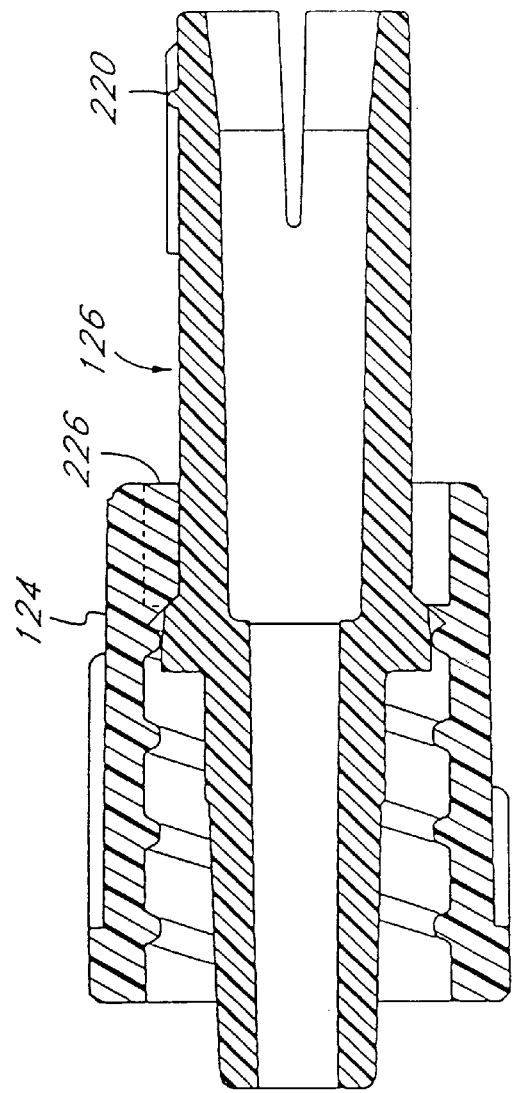
Fig. 14a
Fig. 14b

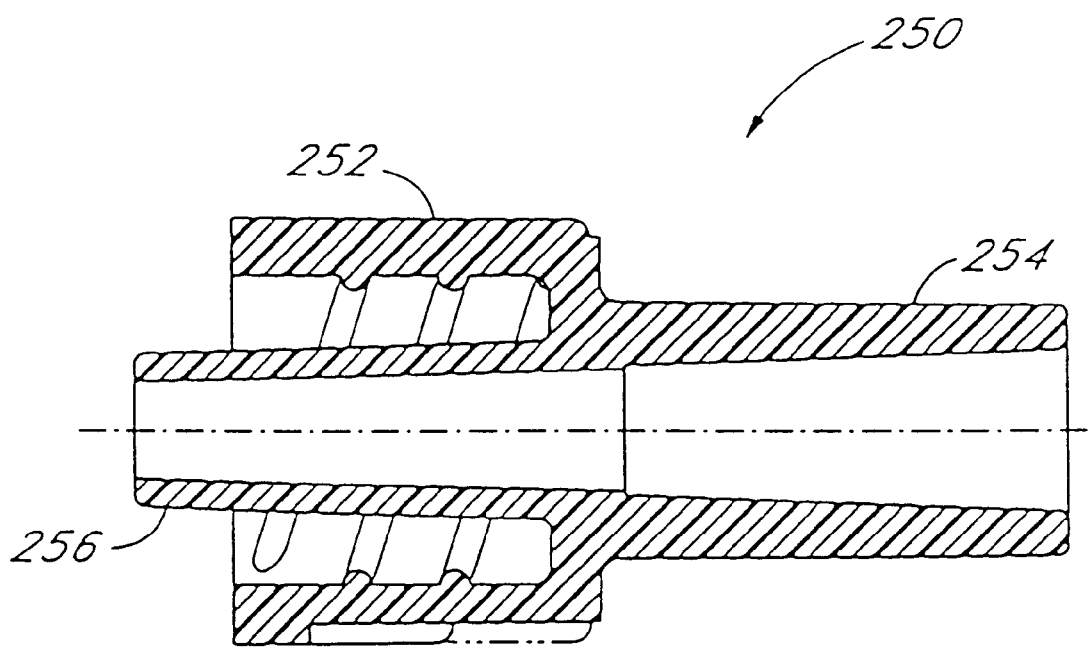

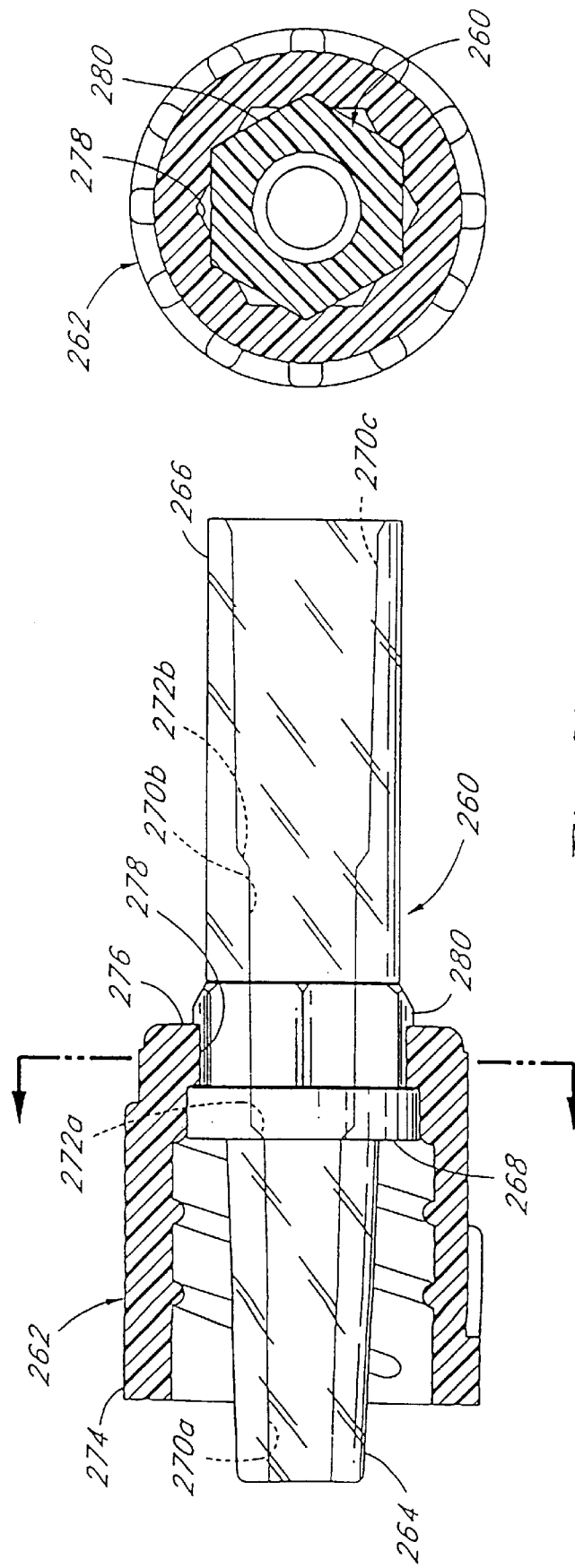

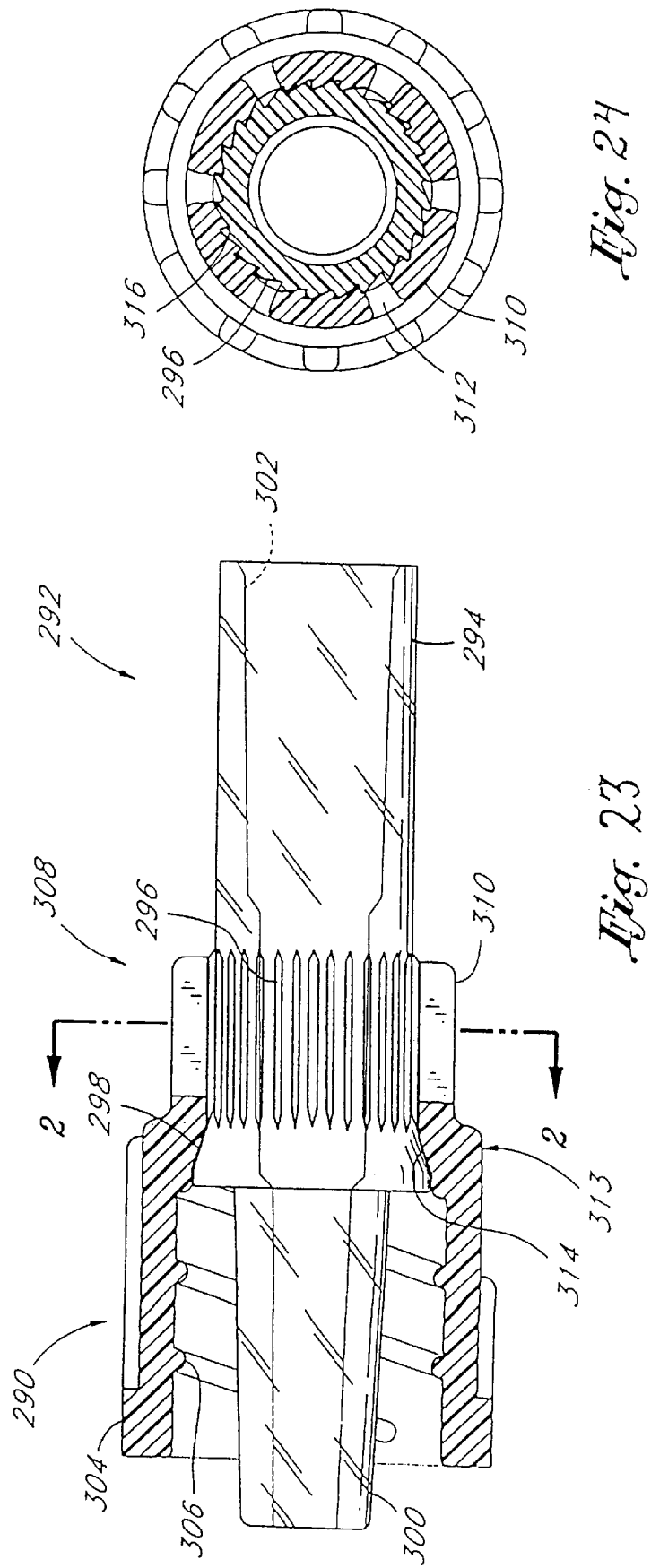

MEDICAL LUER CONNECTION HAVING PROTECTIVE CAP WITH CRUSH RIB

CROSS REFERENCES TO RELATED APPLICATIONS

The present application is a continuation-in-part of U.S. patent application Ser. No. 08/431,073, filed on Apr. 27, 1995, now U.S. Pat. No. 5,620,427, and entitled LUER LOCK SYSTEM, and which is expressly incorporated herein by reference.

FIELD OF THE INVENTION

The present invention pertains to a luer-lock connector system for medical devices and, more particularly, to a protective cap for use with a luer-lock connector.

BACKGROUND OF THE INVENTION

Medical connectors for intravenous applications often utilize standard luer connectors having a tapered tubular body which fits into a tapered socket or luer adapter of a second body to provide a frictional seal between two fluid conduits.

Early embodiments of the luer connector included a tapered male nose portion adapted to fit within a tapered female receiver, the two pieces being locked together with a threaded hub engagement. The hub was typically rotationally coupled to the male portion so that assembling the luer connector together by twisting the hub resulted in the twisting of the male portion, sometimes establishing a reverse torque within one or both of the fluid conduits extending from the connector components. This reverse torque tended to twist the fluid conduits connected to one or both of the connector components which can cause the loss of patency of the I.V. site, or other complications associated with twisted conduits.

To remedy this situation, the next generation of luer locks incorporated a separate rotatable hub or sleeve having internal ribs for mating with external splines on either the male or female luer connector body. The hub typically slides axially and freely spins over a first one of the luer components and has an internal stop which cooperates with an external stop on the first luer component. When the male and female components are brought together, the hub engages an external projection or thread on the second luer component and, due to the engaging stops, urges the male component into sealing engagement with the female component. Prior hubs assemble onto the male component from the nose or distal end, and are forced over a stop ring or other structure on the tubular male component. Jamming the hub onto the male component in this manner often results in hoop stress fractures of either piece.

The hub on this type of connector may have two axial positions: a distal, freely rotatable position which allows relative to hub to first luer component rotation, and a proximal position in which the hub and first luer component are rotationally locked. This rotational coupling is typically provided by internal ribs on the internal hub engaging projections on the exterior surface of the first luer component when the hub is in the proximal position. See, e.g., U.S. Pat. No. 4,607,868 to Harvey et al. The rotational lock is provided to assist in breaking the luer connection between the tapered male and female surfaces. Indeed, some luer connections are connected for extended periods of time resulting in the male and female surfaces of the luer connection becoming essentially glued together.

Although the hub in the prior art connectors is tightened to join the male and female components together, the hub has a tendency to rotate in a reverse direction increasing the risk of disengagement of the medication line. To prevent this from happening, nurses sometimes apply tape over a tightened hub to prevent it from rotating relative to the male and female luer connection.

Another problem with the aforementioned hub-type luer connection arises from the internal ribs on the hub and the external projections on the forced luer component to provide rotational locking engagement. The operator occasionally has difficulty sliding the hub proximally over the first luer component to engage the projections because the ribs and projections or circumferentially aligned and in some rotational positions interfere with each other. In addition, the outer diameter of the hub is large enough to interfere with the appropriate percutaneous entrance angle for an I.V. needle, particularly in the pediatric applications. The use of hub-type luer connectors on these sensitive applications may be inappropriate, and in a simple slip luer is commonly used. This necessitates maintaining an inventory of both types of luer connectors.

Thus, there is a need for an improved connector in which the risk of inadvertent hub rotation is minimized by a relatively high anti-rotation friction, and the other limitations of the prior art connectors are overcome. There is also a need for a connector in which the hub can be pulled away from the luer to permit slip connections.

Yet another problem with the aforementioned luer-lock connectors arises when the male and female surfaces of the individual luer connector components are separated and exposed. In this situation, both the exposed connection regions and internal portions of the male component and particularly the female component may be damaged, contaminated or otherwise affected. Prior art connectors utilized various methods of protecting these surfaces, however, they were ineffective or were not properly retained on the luer connector and were easily removed or dislodged. In addition, the prior art protective caps, if used, did not allow sterilization of the connector component.

Thus, there is a need for an improved protector cap for use with luer connectors which protects the luer components from damage and contamination. In addition, there is a need for a protective cap which minimizes the risk of inadvertent dislodging or removal. There is also a need for protective cap which allows the luer component to be sterilized while remaining protected by the cap.

SUMMARY OF THE INVENTION

The present invention provides a protective cap for use with a luer component having an elongated tubular body with external threads formed on a proximal tubular end. The protective cap includes a tubular body having an inner surface with one closed end. Internal threads are formed on the inner surface and are sized and shaped to engage with the external threads on the luer component. The threads are thus used to coupled the protective cap with the luer components. A crush thread is formed adjacent a portion of the inner threads and protrudes radially inwardly from the inner surface of the protective cap. The crush thread is configured for engagement with the external threads on the luer component, such that when the protective cap is threaded onto the luer component, the crush thread frictionally interferes with the external threads.

In another broad aspect of the present invention, the protective cap further includes a sealing ring which extends inwardly from the closed end and is configured for contacting and sealing against the proximal end of the luer connector. The sealing ring has a cross section which tapers radially inward for penetration into a central lumen within the luer component. As the protective cap is threaded onto the luer component, the external threads engage the crush thread creating frictional engagement. In addition, as the protective cap is drawn inwardly over the proximal end, the sealing ring is drawn into the central lumen thus engaging the proximal end and providing a sealing surface.

The protective cap is made from a medical grade plastic which is preferably softer than the external threads on the luer component. In this way, the crush thread is deformed when engaged with the exterior threads to create a frictional interference. More particularly, as the external threads on the proximal end of the luer component contact the crush thread within the protective cap, the crush thread is deformed. This deformation increases the surface area which actually contacts the external threads and thus increases the physical and thus frictional interference. In this way, as the protective cap is threaded over the luer component, a frictional interference is created which resists the decoupling of the protective cap.

In yet another aspect of the present invention, a medical connector is provided which includes an elongate tubular body having a central lumen which extends axially therethrough. A hub is provided which is movable axially over the tubular body. The hub and the tubular body both include complimenting frictional engagement surfaces which cooperate to resist rotation of the hub with respect to the tubular body when the medical connector is assembled. More specifically, the hub is movable between a proximal position in which the hub is rotationally locked with respect to the tubular body, and a distal position in which the frictional engagement surfaces contact each other to resist relative rotation of the hub and tubular body. When the hub is at an intermediate position, in between the proximal and distal position, the hub is freely rotatable about the tubular body.

The tubular body includes at least one radially, outwardly extending projection which mates with an axially extending channel on the interior surface of the hub so that the hub is rotationally locked so that it remains axially movable with respect to the tubular body when the projection is within the channel. This corresponds to the proximal position of the hub over the tubular body. Preferably, five projections are provided to minimize the occurrence of rotational skipping of the hub with respect to the tubular body. All of the projections are preferably positioned within a single hemisphere (side) of the tubular body to facilitate manufacturing.

In a preferred form, the frictional engagement surfaces comprise inclined angular surfaces; one around the exterior of the tubular body and one within the interior of the hub. Both these annular surfaces are preferably inclined radially outward in the distal direction, the inclination being within the range of about 1 percent to about 15 percent respect the longitudinal axis of the tubular body. The tapered engagement surfaces are configured so that a hub can be positioned at a first distal position where the engagement surfaces are in contact, and then can be moved to a second distal position disposed distally from the first distal position. The amount of axial movement of the hub from the first distal position to the second distal position determines the level of frictional engagement between the engaging surfaces.

BRIEF DESCRIPTION OF THE DRAWINGS

FIG. 1 is a cross-sectional view of a two-piece luer-lock connector and protector cap;

FIG. 2 is a cross-sectional view of the two-piece luer-lock connector engaged with a female luer components and showing a hub in the distal, anti-rotation position;

FIG. 3 is a cross-sectional view similar to FIG. 2 with the hub shown in a proximal position in which the hub is rotationally coupled to an male luer component;

FIG. 4 is an elevational view of the two-piece luer-lock connector taken along line 4—4 of FIG. 3;

FIG. 10 is a cross-sectional view of another two-piece luer-lock connector and protector cap embodiment;

FIG. 11 is a detailed view of an area of engagement between a male luer component and a rotatable hub shown in FIG. 10;

FIG. 12a is a partial plan view of a proximal end of the male luer component showing a spline arrangement as seen along line 12—12 of FIG. 10;

FIG. 14a is a cross-sectional view of a hub advancing distally over an alternative luer component;

FIG. 14b shows the hub advanced distally onto the male luer component of FIG. 14a;

FIG. 18 is a cross-sectional view of a preferred protector cap having a sealing ring shown engaged with a female luer component;

FIG. 18a is a cross-sectional end view of the protector cap of FIG. 18 taken along line 18a—18a;

FIG. 20 of a cross-sectional view of a one-piece male luer component and hub;

FIG. 21 is a cross-sectional view of a two-piece luer-lock connector having a hex coupling between the hub and male components;

FIG. 22 is a cross-sectional view of the hex coupling taken along line 22—22 of FIG. 21;

FIG. 23 is a cross-sectional view of a two-piece luer-lock connector having a ratchet coupling between the hub and male components; and FIG. 24 is a cross-sectional view of the ratchet coupling taken along line 24—24 of FIG. 23;

DETAILED DESCRIPTION OF THE PREFERRED EMBODIMENTS

Figure 5:
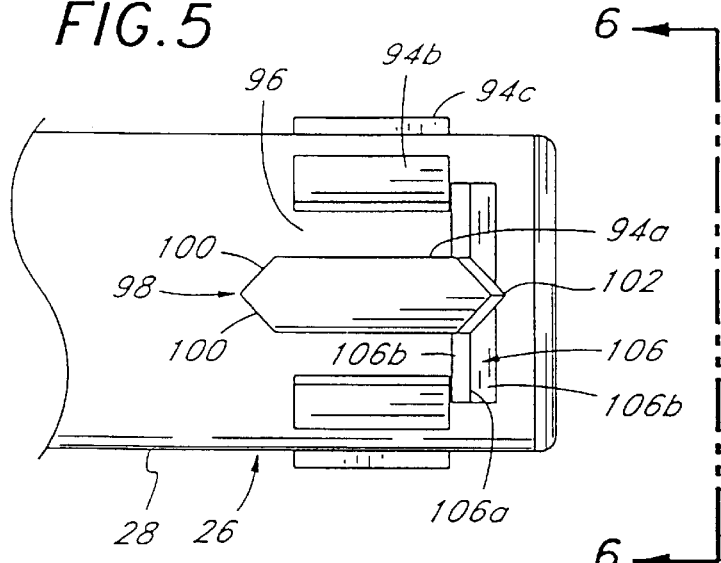
FIG. 5 is a partial plan view of a proximal end of the male luer component as seen along line 5—5 of FIG. 2.

FIG. 1 is a cross-sectional view showing a two-piece medical luer-lock connector 20 engaged by a protector cap 22. The two-piece luer-lock connector comprises a hub 24 and a tubular male luer component 26. Although the present invention will be described in terms of the two-piece luer-lock connector 20 comprising a hub and male luer connector, the hub could also be associated with a female luer connector, as will be readily apparent to one of skill in the art. In most cases, however, the hub 24 is associated with a proximal component of a luer connector, the proximal direction being away from the patient or application site. One particularly useful application for the present invention is for attaching an intravenous fluid supply line to an IV catheter at an infusion site.

In the illustrated embodiment, the male luer component 26 comprises an elongate tubular body having a proximal tubular section 28, a tapered nose 30, and a tapered shoulder 32 disposed therebetween. A cylindrical step 33 is provided on the tapered nose 30 just distal from the tapered shoulder 32. A central lumen consists of a distal conduit 34 transitioning at a step 36 to a proximal conduit 38. The proximal conduit 38 terminates in a flared mouth 40 for receiving a flexible delivery hose (not shown) which may be inserted all the way to the stop 36 and glued or otherwise adhered into place.

Figure 7:
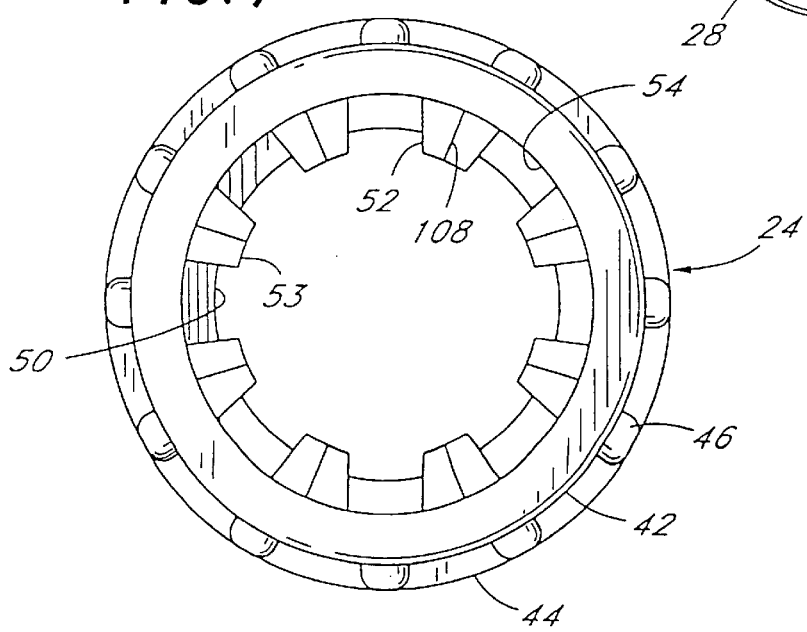
FIG. 7 is an end elevational of the hub of a two-piece luer-lock connector.

The hub 24 comprises a generally tubular sleeve having a proximal cylindrical exterior surface 42, a distal annular flange 44, and a series of axially extending grip rails 46, as best seen in FIG. 7. The hub 24 has three distinct interior surface regions. A first distal region includes single or multiple internal threads 48. The internal threads 48 may be standard ISO threads or may comprise helical grooves termed sometimes "oversized threads." The proximal end of the distal region terminates at an anti-rotational friction enhancing structure such as an annular internal ramp 50. Finally, a proximal region includes a plurality of radially, inwardly directed ribs 52 separated by channels 54. The functions of the internal surfaces of the hub 24 will be described more fully below.

Male Luer Component Breather Cap

The present invention is preferably provided prior to use with a protector cap 22. As seen on an alternative cap 22' in FIG. 9, cap 22 includes a plurality of end projections 56 which create a gap 58 (see FIG. 1) between the protector cap 22 and the male luer component 26 for ease of priming the device when the cap is in place, the small gap presenting a tortuous path for bacteria after sterilization. More particularly, the protector cap 22 is defined by a closed end portion 60 and an engagement tube portion 62 separated by an annular flange 64 which helps to prevent contamination of the tortuous path. An interior wall 66 is tapered at approximately the same angle as the tapered nose 30 of the male component 26. In one embodiment, the interior wall 66 is formed with a draft of approximately 1° with respect to a central axis, while the nose 30 has a total taper of 0.060 in/in, which corresponds to an angle of 1.7° adjacent the interior wall 66. The outer diameter of the engagement tube 62 is slightly greater than the inner diameter of the internal threads 48 of the hub 24. Thus, when the cap 22 is inserted around the tapered nose 30 and within the hub 24, it is frictionally engaged by the internal threads 48 and protects the nose. Further, the end projections 56 create the aforementioned gap 58 to allow the passage of sterilization gas or other media. The protector cap 22 additionally has a plurality of axially extending grip rails 68 for facilitating the removal from the two-piece luer-lock connector 20.

In certain embodiments, the hub 24 is eliminated and an alternative protector cap is used which has a smaller internal diameter for interfering with the step 33 on the tapered nose 30. In this alternative embodiment, the inner circumference of the protective cap may have inwardly directed ribs for interfering with the step 33, or, the step 33 may be formed with a plurality of separate ribs for interfering with a continuous inner diameter of the protective cap.

In all of the protective cap embodiments, a small tortuous passage is provided through the inner lumen of the male component 26 and around the proximal end of the protective cap 22 by virtue of the end projections 56 and gap 58. Thus, the assembled male component 26 and protective cap 22 can be sterilized allowing gases to flow therebetween. However, after sterilization, an open, yet highly tortuous path is provided between the protective cap 22 and inner lumen of the male component 26. This tortuous path helps prevent contamination of the male luer component 26.

Luer-Lock Connector

Now with reference to FIGS. 2 and 3, the two-piece luer-lock connector 20 is shown coupled to a second tubular body, in this case a female luer component 70. Luer component 70 may provide communication with a segment of IV line, medical device, infusion needle, or other structure as is understood in the art. The female luer component 70 comprises a distal tubular portion 72 and larger diameter proximal tube 74 provided with one or more external thread segments 76. The external thread segments 76 are sized and configured to threadingly mate with the internal threads 48 of the hub 24.

The proximal tube 74 has an inner lumen 78 which is tapered outwardly in the proximal direction. The taper angle of the wall of lumen 78 preferably approximates the taper angle of the nose 30 of the male luer component 26. Thus, as seen in FIG. 2, the tapered nose 30 fits within the lumen 78 and the hub 24 threadingly engages the exterior thread segments 76 to lock the male and female luer components 26, 70 together in sealing engagement.

Distal axial travel of the hub 24 is limited with respect to the male luer component 26 by the engagement of the tapered shoulder 32 on male luer component 26 and internal annular ramp 50 on hub 24. Thus, the tapered nose 30 and inner lumen 78 are forced into frictional fluid-sealing engagement by rotation of the hub 24 with respect to the male luer component 26. Alternatively, the tapered nose 30 may be engaged with the inner lumen 78 without using the hub 24 by simply advancing the male luer component 26 axially toward the female component 70. A pair of opposed wings 80 or other gripping structures are preferably provided on the female luer component 70 as torque grips for disengaging the male and female luer components, as will be explained more fully below. The female luer component 70 further includes a second lumen 82 within the distal tubular portion 72 and an inner throughhole 84 for providing communication between the first and second lumens 78, 82.

Hub/Male Component Anti-Rotation Structure

In one particular embodiment, the present luer-lock connector can provide for an anti-rotation feature for the hub 24 with respect to the male luer component 26. More specifically, as the hub 24 advances distally over the external thread segments 76, the engagement of the tapered shoulder 32 and internal ramp 50 causes the nose 30 to sealingly engage the first lumen 78. At some point, the engagement between the nose 30 and inner lumen 78 halts further distal movement of the male luer component 26. Further rotation of the hub 24 causes the cooperating ramped surfaces 32, 50 to slide axially relative to each other to produce a relatively tight friction fit between the hub 24 and friction enhancement surface 32.

Figure 8A:
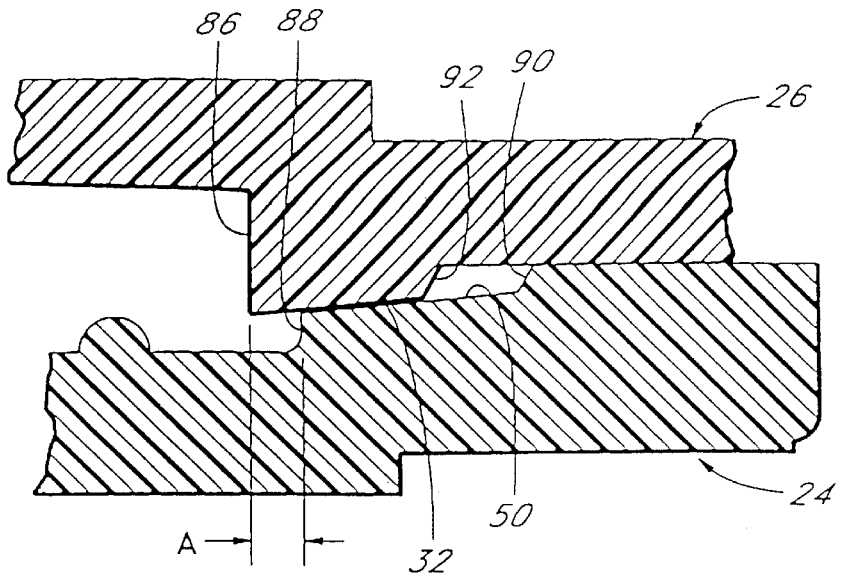
FIGS. 8a–8c shown several stages of engagement between friction surfaces of the hub and the male luer component.
Figure 8B:
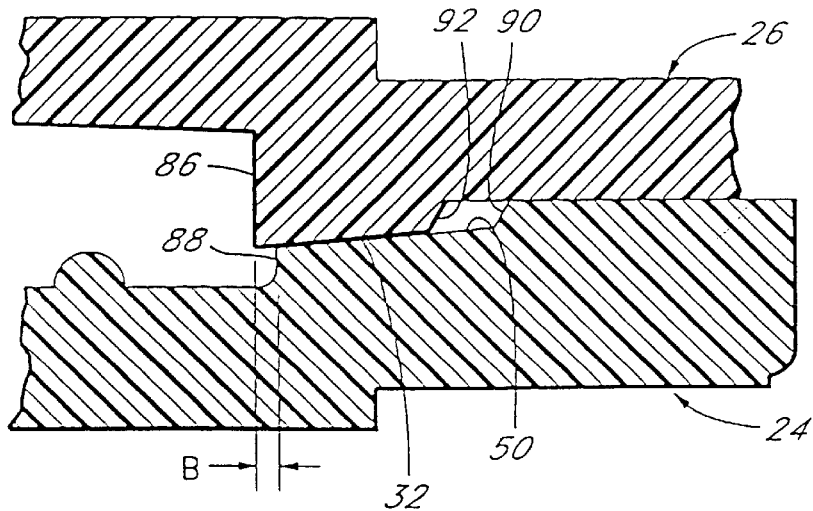
Figure 8C:
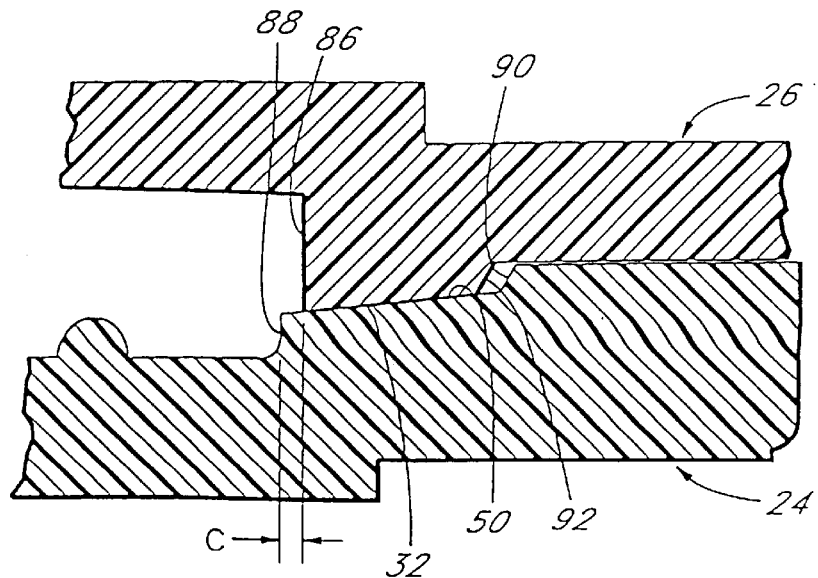

With specific reference to FIGS. 8a–8c, this relative sliding movement is shown. For example, FIG. 8a illustrates a situation when the tapered engagement surfaces 32, 50 are in simple contact without substantial frictional engagement therebetween. This situation might be when the hub 24 has been sufficiently rotated to bring tapered nose 30 into contact with the inner lumen 78. At this point, an exterior step 86 of the male luer component 26 at the distal end of surface 32 is disposed distally by a distance A from an internal step 88 of the hub 24 at the distal end of surface 50.

FIG. 8b illustrates a position wherein the hub 24 has been rotated further over the male luer component 26 causing the frictional engagement surfaces 32, 50 to slide axially relative to one another. At this point, the step 86 is disposed a smaller distance B distally from the step 88 of the hub 24. Finally, in FIG. 8c, the hub 24 has been rotated farther over the exterior thread segment 76 of the female luer component 70 to force the frictional engagement surfaces 32, 50 to slide even more so relative to each other. At this point, the step 86 is disposed proximally to the step 88 by a distance C. Further tightening of the hub 24 will cause a hard stop 90 to contact a proximal stop surface 92 on the male luer component 26. The stop surfaces 90, 92 may be disposed at approximately 45° angles to the longitudinal axis to prevent further relative axial movement and prevent fracture of either the male luer component 26 or hub 24 from overtightening.

As will be apparent, in all of the axial positions of hub 24 in FIGS. 8a–8c, the hub is frictionally rotationally engaged with the male luer component 26. Thus, the present invention provides an anti-rotation friction throughout an axial range of travel in a manner that minimizes the risk of reverse rotation and loosening of the hub throughout various rotational positions of the hub 24. The relative axial position of the hub 24 with respect to the male luer component 26 is determined by the amount of tightening torque applied thereto, which can differ from operator to operator. The present invention accommodates different application forces by providing an anti-rotation frictional engagement over a range of different tightening torques.

The taper angles of the engagement surfaces 32, 50 are thus selected to provide frictional engagement over a range of axial travel after the point at which the two surfaces initially contact. The shallower the taper angles, the greater the axial travel that can be accomplished between the hub 24 and male luer component 26, within given elastic deformation limits of the hub 24. A relatively steep taper angle, such as is present for engaging thread surfaces, will tend to minimize the axial range of frictional engagement.

In terms of percent of inclination (100% being a 45° taper) the engagement surfaces 32, 50 are preferably identically tapered within the range of from about 1% to about 15% with respect to the longitudinal axis of the tubular bodies. Preferably, the engagement surfaces 32, 50 are typically tapered less than about 10% and within a range of about 2% to about 8%, with a preferred range of between 2% to 6% and an optimum taper of about 5% with respect to the longitudinal axis of the tubular bodies. In one preferred embodiment, with an optimum engagement surface incline of 5%, the axial travel is within the range of from about 0.08 and about 0.18 inches.

Hub/Male Luer Component Rotational Coupling Structure

In accordance with another aspect of the present invention, the present two-piece luer lock connector 20 provides an improved structure for rotationally locking the hub 24 to the male luer component 26. With reference now to FIGS. 2–7, the radially inwardmost edges 53 of the radially inwardly extending ribs 52 on the hub 24 define a circle having approximately the same diameter as the proximal tubular portion 28 of the male luer component 26. The proximal end of the male luer component 26 includes a series of axially extending splines 94 projecting outward from the tubular portion 28. The ribs 52 are dimensioned to interfit in sliding engagement between the splines 94 along guideways 96. Conversely, the splines 94 extend along the channels 54 between the ribs 52. The circumferential dimensions of the ribs 52 and guideways 96 may provide a slight interference tolerance to indicate when the hub 24 and male luer component 26 are rotationally locked.

Figure 6:
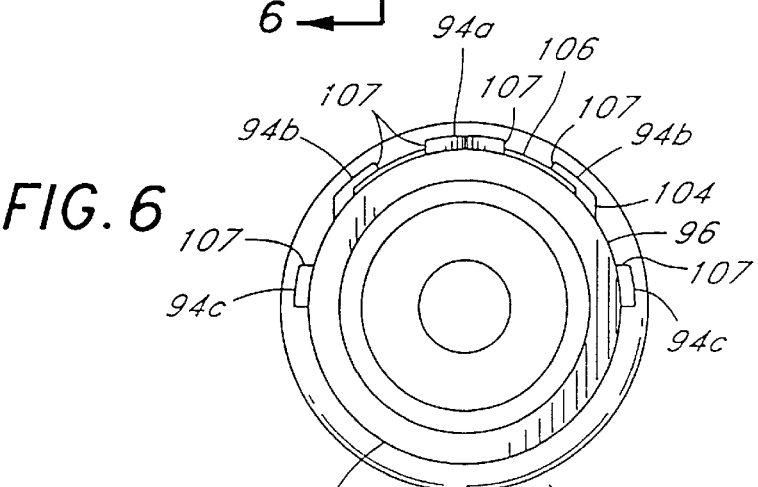
FIG. 6 is an end elevational view of the male luer component taken along line 6—6 of FIG. 5.

With specific reference to FIGS. 5 and 6, the male luer component 26 includes at least a central axially elongated spline 94a, preferably also a pair of intermediate splines 94b disposed on either side of the central spline, and most preferably also a third pair of substantially diametrically opposed splines 94c. The distal end of the central spline 94a includes a point 98 leading to a pair of ramped cam surfaces 100. The proximal end of the elongated spline 94a is preferably tapered radially inwardly in the proximal direction and also tapered circumferentially to produce a point 102.

The second and third pairs of splines 94b, 94c form generally rectangular radial projections with the second splines 94b including angled edges 104 facilitating removal of a forming mold. More specifically, the male luer component 26 is preferably formed by two mating semi-cylindrical half-molds with all of the splines 94 being formed by only one of the two molds. In the illustrated embodiment of FIG. 6, the upper mold would form the splines 94 and thus it can be readily seen that the edges 104 allow the mold to be lifted off cleanly.

In a preferred embodiment, there are at least three spline contact points 107 in either rotational sense to provide tangential strength to avoid stripping by the inwardly directed ribs 52, however, the present invention may comprise only one spline 94. Although the preferred embodiment includes splines 94 on only one circumferential half, it should be noted that splines may be formed all the way around the circumference of the male luer component 26 and still achieve many of the inventive aspects herein.

Rotational Coupling Indicator

To provide tactile feedback for an operator when sliding the hub 24 axially in a proximal direction into the rotationally locked position, a circumferentially formed "speed bump" or ridge 106 is provided on the male luer component 26. As seen in FIGS. 5 and 6, the illustrated circumferential ridge 106 is centered at the elongated spline 94a although it can readily be positioned at other locations around the circumference of tubular body 28 or be formed in a 360° circle to act as a retaining ring. The illustrated ridge 106 extends circumferentially in an approximately 90° arc around the tubular portion 28 and has a radially projected height of at least one-half and preferably nearly two-thirds the height of the splines 94. The circumferential ridge 106 is preferably formed with an apex 106a and a pair of ramped surfaces 106b. As the hub 24 is advanced in the proximal direction, the inwardly directed ribs 52 come in contact with the circumferential ridge 106 and the user experiences a more pronounced drag or frictional engagement between the hub 24 and male luer component 26. The size of the ridge 106 and the preferred connector material allow the hub 24 to be advanced across the ridge and flex without damage to either component. In some cases, extreme tolerances may create an additional interference between the inwardly directed ribs 52 and circumferential ridge 106. The ribs 52, being larger, may shave off or deform a small portion of the ridge 106 resulting in a consistent interference and tactile feedback thereafter. The purpose of the ridge 106 is to provide feedback to indicate to an operator when the hub 24 is axially positioned to achieve optimum rotational locking engagement with the male luer component 26.

Figure 12B:
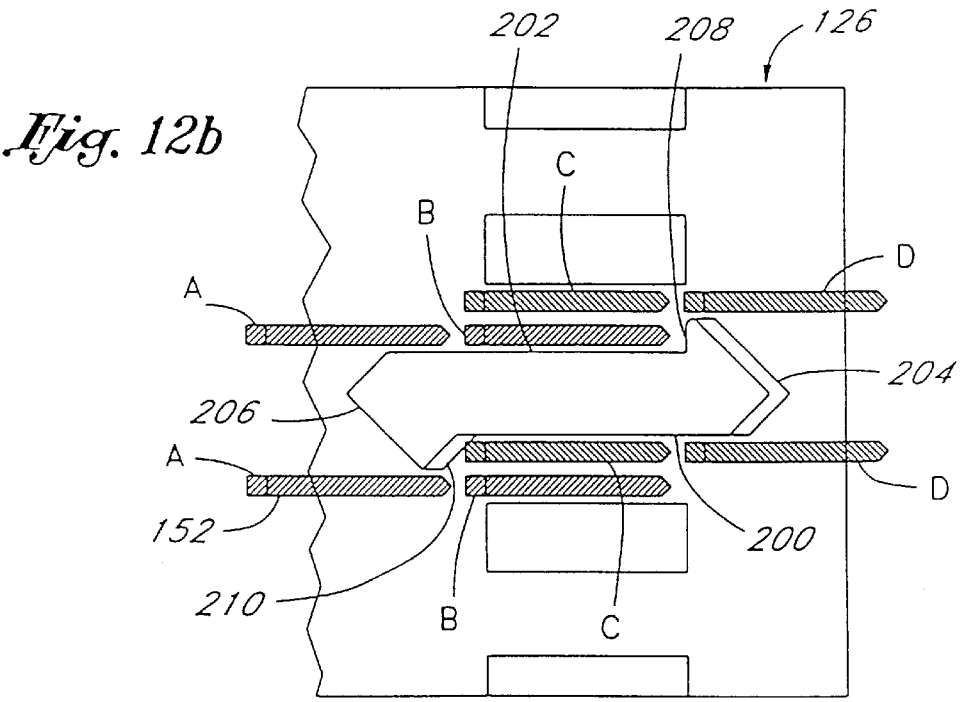
FIG. 12b is a partial plan view of a proximal end of the male luer component showing and alternative spline arrangement and taken along line 12—12 of FIG. 10.

In an alternative embodiment, the diameters of the inwardly directed ribs 52 and proximal tubular portion 28 may be such that there is a net tolerance in the region of the splines 94 to provide this tactile feedback, instead of providing a circumferential ridge 106. Additionally, FIG. 12b illustrates a "keyed" version wherein a stepped spline positively stops the hub in a position coupling the hub and male component. The hub may be removed by rotation with respect to the male component. Other tactile feedback structures for indicating the axial position of the hub 24 can be readily envisioned by one of skill in the art in view of the disclosure herein.

Hub Removal

As there is no travel limiting structure in the proximal direction from the splines 94 and ridge 106, the hub 24 can be completely removed from the proximal end of the male luer component 26. The hub 24 can thus be slid proximally along a supply line (not shown) to remove it from the immediate connector site. This may be advantageous in neo-natal, pediatric or other applications where the relatively large diameter of the hub 24 is an impediment to proper positioning of the connector and associated medical components, and may cause a pressure point on the skin.

Hub/Male Component Rotational Registry

The cam surfaces 100 on the distal end of the elongated central spline 94a ensure the proper rotational registry of the hub 24 with the splines 94. The proximal ends of the ribs 52 are tapered at 108 to form guide points. As the hub 24 is slid proximally along the male luer component 26, the distal point 98 on the central spline 94a will initially contact the inwardly directed ribs 52. The ribs 52 may either be aligned with the channels 96 or with the central elongated spline 94a. In the latter case, the guide points 108 will contact one or the other of the cam surfaces 100 on either side of the proximal point 98, and the hub 24 will be caused to rotate into proper rib/spline alignment.

Similarly, distal travel of the hub 24 onto the male component 26 may initially bring point 102 into contact with a corresponding point on the distal end of one of the ribs 52. Further distal advancement of the hub 24 will cause an appropriate rotational alignment of the ribs 52 with channels 96.

Specific Embodiment

A particular embodiment of the present two-piece luer connector 20 will now be described. The particular dimensions can be modified to suit the needs of any particular use environment, as will be understood by one of skill in the art. In this particular embodiment, the male component 26 has an overall length of about 1.12 inches, with an outside diameter of the proximal tubular portion 28 being approximately 0.236 inches. The step 86 on the tapered shoulder begins at approximately 0.435 inches from the distal tip of the tubular body 26 and the tapered surface 32 has an axial length of approximately 0.065 inches. The small diameter on the proximal end of the tapered step 32 is approximately 0.269 inches, while the large diameter is approximately 0.275 inches of the hub 24.

In one embodiment, hub 24 has an overall length of approximately 0.54 inches, and the inwardly directed ribs 52 define a cylinder having a diameter of approximately 0.240 inches, resulting in a about 0.004-inch nominal clearance between the ribs and the proximal tubular portion 28. The annular inclined surface 50 on the hub 24 preferably has an axial length of approximately 0.088 inches, a small diameter of approximately 0.266 inches, and a large diameter of approximately 0.279 inches.

The ribs 52 may have an axial length of approximately 0.127 inches, while the axial length of the intermediate and diametrically opposed splines 94b, 94c have an axial length of about 0.123 inches. The central spline 94a has an axial length from distal point 98 to proximal point 102 of approximately 0.223 inches. The circumferential ridge 106 preferably extends 90° around the male tubular portion 28 and has a radial height of approximately 0.008 inches at its apex 106a. The hub 24 has a preferred nominal wall thickness of approximately 0.039 inches, while the male luer component 26 has a minimum wall thickness in the proximal tubular portion 28 of approximately 0.047 inches.

Materials

The components of the two-piece luer connector 20 are preferably injection molded using known biocompatible materials. More specifically, the materials are preferably resistant to corrosion from chemicals, such as alcohol and/or lipids, common in medical environments. For example, ABS (available from BASF under the trade name TERLUX™) may be used for the hub 24 and acrylic, polycarbonate or other material for the male and female components 26, 70. Polypropylene is used for the protector cap 22 to allow for deformation from the tolerance interference with the male luer component 26 during assembly and to enhance resistance therebetween, preventing the cap from falling off. The materials used for the male component 26 and hub 24 are preferably dissimilar to enhance the frictional engagement between the surfaces 32, 50.

Alternative Anti-Rotation Structure

In an alternative embodiment to the frictional engagement between the surfaces 32, 50, the hub 24 and male luer component 26 may be provided with a ratchet-type engagement. In this embodiment, either the hub 24 or male luer component 26 is provided with one or more detents, which engage grooves in the opposite component to securely lock the hub relative to the male luer component. Such a ratchet configuration is shown and described with reference to FIGS. 19 and 20. Other types of complementary surface structures can be readily provided which, through elastic deformation during tightening, provide a relatively high resistance to reverse hub rotation.

Operation of Luer-Lock Connector of FIGS. 1–8

In operation, the nose 30 of the male luer component 26 is inserted within the tapered lumen of the female luer component 70. The hub 24 is advanced in a distal direction so as to engage the inwardly extending threads 48 with the external thread segments 76. The hub 24 is then rotated relative to both the male and female components 26, 70 to advance over the external thread segments 76 without applying a torque to any hoses connected to the male and female components. At some point, the tapered nose 30 will be forced into sealing engagement with the lumen 78 and the male luer component 26 will experience resistance to further advancement into the female luer component 70. Depending on the tightening torque applied by the user, the hub 24 may be advanced a short distance further causing the tapered engagement surfaces 32, 50 to slide relative to each other, as previously described. Thus, the male and female luer connectors 26, 70 are firmly attached, and the hub 24 is frictionally rotationally engaged on the tapered annular shoulder 32. To remove the hub 24, the operator grasps the wings 80 or other structure of the female luer component 70 and rotates the hub to disengage the engagement surfaces 32, 50 and reverse the internal threads 48 from the external thread segments 76.

The amount of torque required to remove the hub 24 is sufficient to minimize the risk of inadvertent hub rotation, and may in some embodiments be even slightly greater than the torque applied in tightening. This is due to the greater coefficient of static friction between the tapered engaging surfaces 32, 50 achieved by the present invention than their relative coefficient of sliding friction.

To illustrate this point, tests were made on various prior art luer connectors to determine the amount of torque required to untwist a sleeve or hub after tightening a predetermined amount. During the test procedure, all of the fittings were dry and tightened to a torque of 16 in-oz. The connector components embodying the present invention were injection molded from K resin from Phillips for the hub 24, and G-20 Hiflow acrylic from Cyro Industries for the male and female components 26, 70. The specific materials may be otherwise, but are preferably resistant to corrosion from chemicals, such as alcohol and/or lipids, common in medical environments. The surface 32 and surface 50 were each inclined at an angle of 5° from the longitudinal axis of the connector. Five different trials were staged to determine the torque required to disassemble the hubs from the various fittings. Finally, an average of the five trials is given. The results appear below in Table 1.

TABLE 1

Comparative Disassembly Torques for Luer Hubs (in.-oz.)

| | | | Company | | | | | |
|---|---|---|---|---|---|---|---|---|
| | Abbott | Abbott | Baxter (new) | Baxter (old) | Borla | IVAC | Siemens | tr)d |
| 1 | 13 | 10 | 5.5 | 5.5 | 8 | 9.5 | 6 | 5 |
| 2 | 11 | 9.5 | 5 | 5.5 | 8.5 | 10 | 5.5 | |
| 3 | 11 | 9.5 | 5.5 | 5.5 | 9 | 11.5 | 4.5 | |
| 4 | 11 | 9 | 5.5 | 4.5 | 8 | 11 | 7 | |
| 5 | 10.5 | 7 | 5.5 | 5.5 | 8 | 20 | 6.5 | 5 5 |
| Total | 56.5 | 45 | 27 | 26.5 | 41.5 | 62 | 29.5 | 8 |
| Average | 11.3 | 9 | 5.4 | 5.3 | 8.3 | 12.4 | 5.9 | 8 |

After untightening of the hub 24 from the surface 32 of the male luer component 26, the hub is in a position enabling it to be freely rotated with respect to the male luer component. Although not shown, this position is somewhere between the illustrations of FIGS. 2 and 3, with the ribs 52 between the tapered shoulder 32 and the splines 94. In a more proximal position of the hub 24, the axial ribs 52 are in registry with the splines 94 to rotationally lock the hub with respect to the male luer component 26. The larger diameter hub 24 increases the torque available to unlock the male luer component 26 from frictional engagement with the female luer component 70. This is shown in FIG. 3. Finally, as described above, the hub 24 may be retracted in a proximal direction completely from the male luer component 26 in a still further position along the fluid conduit.

Alternative Protective Cap

Figure 9:
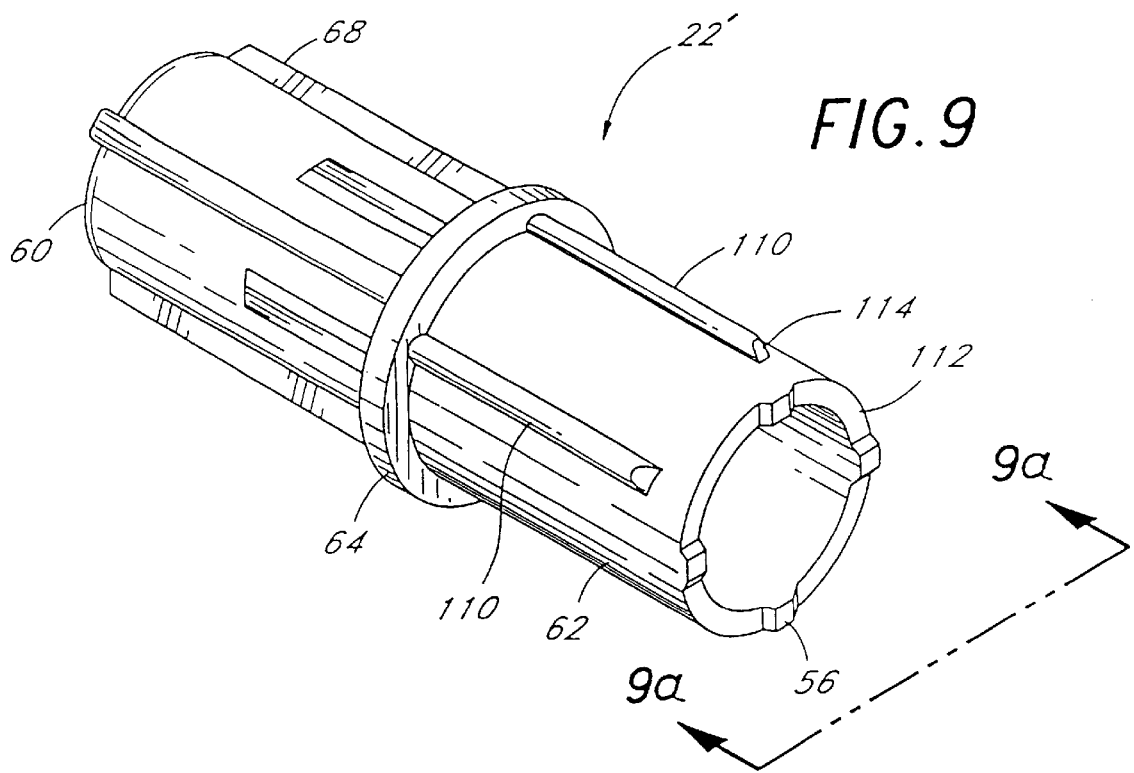
FIG. 9 is a perspective view of a preferred protector cap for the two-piece luer-lock connector.
Figure 9A:
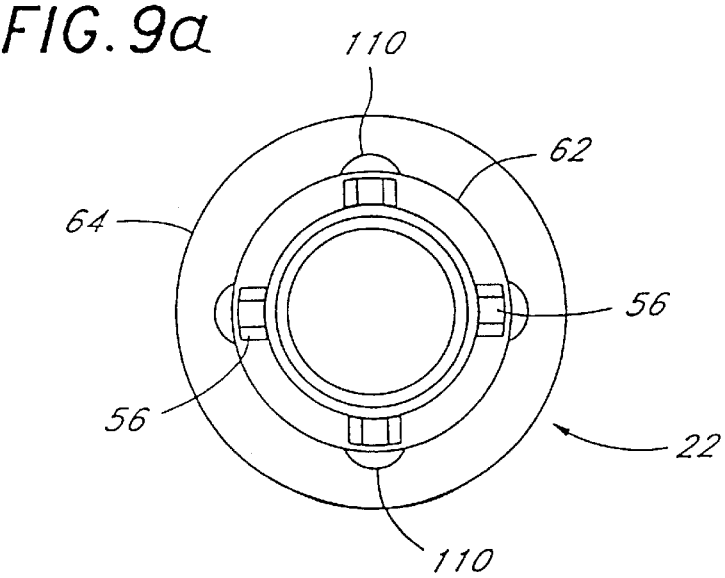
FIG. 9a is an elevational view of an end of the protector cap taken along line 9a—9a of FIG. 9.

The protective cap 22 previously disclosed for mating with the male luer component 26 included a smooth outer engagement surface 62. FIGS. 9 and 9a illustrate an alternative protective cap 22' which includes a series of outwardly directed ribs 110 on the cylindrical engagement portion 62. The ribs 110 are provided to engage the inwardly directed threads on the hub of the present luer connector. This engagement is illustrated in FIG. 10, as will be described below. The ribs 110 extend from the annular flange 64 toward a proximal open end 112 and terminate at ramped surfaces 114. The ribs 110 are preferably rounded in cross-section. It has been recognized that the material of the protector cap 22', preferably polyethylene, shrinks during exposure to the sterilization environment. In contrast, the materials of the male luer connector and hub are less susceptible to dimensional changes during sterilization. Thus, an interference fit provided between a smooth engagement portion 62 and inwardly directed threads 48 prior to sterilization leads to a relatively loose fit after sterilization. Unfortunately, attempts to solve this problem by increasing the diameter of the tubular portion 62 prevents initial engagement between the protective cap 22 and hub 24. Thus, the present invention contemplates providing the axially directed ribs 110 to allow for an increased initial interference fit between the ribs and the inwardly directed threads of the hub. After sterilization, the protective cap 22' has undergone some shrinkage, but the ribs 110 still provide a sufficient frictional engagement with the inwardly directed threads of the hub to retain the protective cap over the nose of the male luer component.

Alternative Luer-Lock Connector

FIG. 10 is a cross-sectional view showing an alternative two-piece medical luer lock connector 120 engaged by the aforementioned protector cap 22'. The two-piece luer lock connector 120 comprises a hub 124 and a tubular male luer component 126. The male luer component 126 comprises an elongate tubular body having a proximal tubular section 128, a tapered nose 130, and a tapered shoulder 132 disposed therebetween. A central lumen consists of a distal conduit 134, a larger proximal conduit 136, and a step 138 disposed therebetween. The proximal conduit 136 terminates in a flared mouth 140 for receiving a flexible delivery hose (not shown) which may be inserted all the way to the step 138 and glued or otherwise adhered into place.

The hub 124 comprises a generally tubular sleeve having a proximal cylindrical surface 142, a distal annular flange 144, and a series of axially extending short and long grip rails 146a, 146b. The hub 124 includes three distinct interior surface regions. The first distal interior region has single or multiple internal threads 148. The internal threads 148 are preferably standard ISO threads. A proximal end of the distal interior region terminates at an anti-rotational friction enhancing structure such as an annular internal taper 150. Finally, a proximal interior region of the hub 124 includes a plurality of radially inwardly directed ribs 152 separated by channels 154 (see FIG. 13). The functions of the internal surfaces of the hub 124 will be described more fully below.

As mentioned previously, the two-piece luer-lock connector 120 is provided prior to use with the protective cap 22'.

As seen in FIG. 10, the outwardly directed ribs 110 on the protective cap 22' engage with the inwardly directed threads 148 on the hub 124. The slight interference provides a gripping force thus preventing the protective cap 22 from sliding from within the hub 124. The present invention has been designed to provide a consistent grip between the protective cap 22' and hub 124. More particularly, the threads 148 have a predetermined pitch, and the ribs 110 a predetermined length, so that each rib contacts two of the threads at all times. This results in a is eight points of contact between the protective cap 22' and the hub 124 in any rotational orientation therebetween. Thus, even with slight variations in tolerances, there will always be eight points of contact resulting a fairly consistent frictional engagement. In the alternative, an outer cylindrical step 156 on the tubular nose 130 frictionally engages an inner diameter of an alternative protective cap (not shown). This frictional engagement is utilized when the hub 124 is not present.

The two-piece luer-lock connector 120 is adapted to couple to a second tubular body, such as the female luer component 70 shown in FIG. 2. As described previously, the protective cap 22' is removed and the nose 130 of the male luer component 126 inserted within a similarly tapered proximal tube on the female luer component. The hub 124 may be used to axially engage the male luer component 126 with the female luer component. With reference to FIG. 11, the inwardly directed ribs 152 have angled distal surfaces 158 which engage with angled steps 160 on the exterior of the male luer component 126, disposed distally from the tapered shoulder 132. Engagement between the angled surfaces 158 and 160 prevent the hub 124 from sliding in a distal direction relative to the male luer component 126. Thus, the hub is used to displace the male luer component 126 toward the female luer component. In this manner, the tapered nose 130 is engaged within the internal taper of the female luer component. The hub 124 may be utilized to lock the two components together, or may be removed.

As mentioned previously, the female luer component is provided with one or more external thread segments, such as those shown at 76 in FIG. 2. The thread segments are sized and configured to mate with the internal threads 148 of the hub 124. The hub 124 rotates freely over the coupled male and female luer components to advance the internal threads 148 over the external threads of the female luer component. Eventually, the angled distal surfaces of the ribs 152 contacts the angled step 160 on the exterior of the male luer component 126. At this point, the nose 130 is forced into the tapered inner tubular portion of the female luer component. When the nose 130 fits tightly within the tapered lumen of the female luer component, the frictional engagement between the angled surfaces 158, 160 provides a slight antirotation feature for the hub 124 with respect to the male luer component 126. More specifically, the surfaces 158, 160 are preferably angled within the range of about 30° to 60°, and preferably approximately 45°, and undergo a small frictional engagement upon tightening of the hub 124. This minimal frictional engagement helps prevent the hub 124 from coming loose.

The male luer component 126 is also provided with the tapered shoulder 132 at a relatively shallow angle with respect to a central axis to couple with the first-described hub 24. The angle of the tapered shoulder 132 is preferably within the range of 0.5° to 7°. As mentioned previously with respect to the engaging tapered surfaces 32, 50 of the embodiment of FIGS. 1–8, the male luer component 126 is adapted to receive the hub 24. More particularly, the inner frictional engagement surface 50 of the hub 24 is sized to engage the outer tapered shoulder 132 of the male luer component 126. Thus, the aforementioned frictional engagement having a range of axial travel of the hub 24 over the male luer component 126 is provided.

Figure 13:
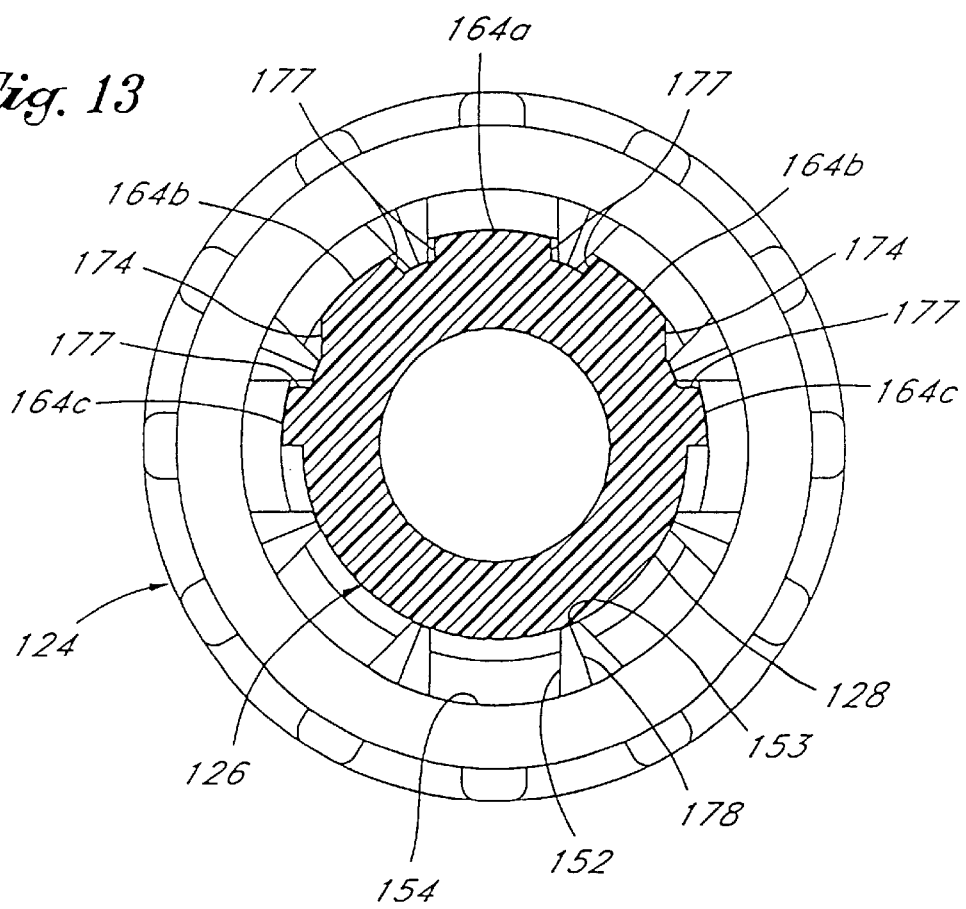
FIG. 13 is a cross-sectional view of the interaction between the proximal end of the male luer component and the rotatable hub of FIG. 10.

As in the previous embodiment, the two-piece luer lock connector 120 includes structure for rotationally locking the hub 124 to the male luer component 126. With reference to FIGS. 12a, 12b, and 13, the radially inner edges 153 of the ribs 152 define a circle have approximately the same diameter as the proximal tubular portion 128 of the male luer component 126. The proximal end of the male luer component 126 includes a series of axially extending splines 164 projecting outward from the tubular portion 128. The ribs 152 are dimensioned to interfit in sliding engagement between the splines 164 along guideways 166. Conversely, the splines 164 extend along the channels 154 between the ribs 152. Alternatively, the circumferential dimensions of the ribs 152 and guideways 166 may provide a slight interference tolerance to indicate when the hub 124 and male luer component 126 are rotationally coupled. In the preferred embodiment, a separate circumferential ridge, or "speed bump," as described below, is provided.

With reference to FIG. 12a, the male luer component 126 includes at least a central axially elongate spline 164a along its exterior surface, and preferably also includes a first pair of intermediate splines 164b disposed on either side of the central spline. Furthermore, a second pair of substantially diametrically opposed splines 164c is also provided. The distal end of the central spline 164a terminates in a point 168 between a pair of ramped cam surfaces 170. The proximal end of the elongate spline 164a is preferably tapered radially inwardly in the proximal direction, and also tapered circumferentially to result in a pointed ramp 172.

The first and second pairs of splines 164b and 164c form generally rectangular radial projections with the intermediate splines 164b including angled edges 174 facilitating removal of a forming mold. More specifically, the male luer component 126 is preferably formed by two mating semi-cylindrical half-molds with all of the splines 164 being formed by only one of the two molds. In the embodiment of FIG. 12a, the upper mold would form the ridges 164 and it can be readily seen that the edges 174 allow the mold to be lifted off cleanly. This arrangement increases the potential mold cavity density in the manufacturing molds. Specifically, the elimination of certain slides used to form undercuts allows the mold cavity density to increase from 32 or 48 cavities per mold to 64 cavities per mold. Each cavity forms an individual part in each mold. It will be readily apparent to one of skill in the art that the increased mold cavity density by a factor of two greatly speeds the manufacturing process, and reduces the expense associated with manufacturing the molds.

In the preferred embodiment, there are at least three spline contact points 177 in either rotational sense to provide tangential strength to avoid stripping the splines 164 by the inwardly directed ribs 152. However, the present invention may comprise only one spline 164. Also, although the preferred embodiment includes splines 164 on only one circumferential half, it should be noted that splines may be formed all the way around the circumference of the male luer component 126 and still exhibit many of the inventive aspects herein.

Tactile feedback for an operator when sliding the hub 124 axially in a proximal direction into the rotationally locked position is provided by a circumferentially formed ridge 176 on the male luer component 126. As seen in FIG. 12a, the circumferential ridge 176 is centered at the elongated spline 164a, although it can be readily positioned at other locations around the circumference of the tubular body 128, or be formed in a 360° circle to act as a retaining ring. The illustrated ridge 176 extends circumferentially in an approximately 90° arc around the tubular portion 128 and has a radially projected height of at least one half and preferably approximately two-thirds the height of the splines 164. In contrast to the previously described circumferential ridge 106 shown in FIG. 5, the circumferential ridge 176 seen in FIG. 12a is formed with a flat apex 176a and a pair of outer ramped surfaces 176b. As the hub 124 advances in the proximal direction, the inwardly directed ribs 152 come into contact with the circumferential ridge 176 and the user experiences a more pronounced drag or frictional engagement between the hub 124 and male luer component 126 due to the increased surface area contact therebetween. The height of the ridge 176 and the preferred connector material allow the hub 124 to advance across the ridge and flex without damage to either component. The ribs 152 may shave off or deform a small portion of the ridge 176, in cases of extreme tolerance interference, resulting in a consistent tactile feedback thereafter. The ridge 176 provides tactile feedback to an operator to indicate when the hub 124 is axially positioned to achieve optimum rotational locking engagement with the male luer component 126. As mentioned previously, other tactile feedback structure to indicate this preferred axial position of the hub 124 over the male luer component 126 is contemplated.

In a comparison of FIGS. 7 and 13, the ribs 152 are narrower than the previously described ribs 52. The radially inward points 153 in contact with the male luer component 126 are thus narrower. The narrower ribs 152 facilitate automated assembly of the hub 124 onto the male luer component 126. It has been discovered through empirical tests that the narrower ribs 152 allow for some rotational movement between the hub 124 and the male luer component 126. Because of this rotational looseness, the ribs 152 may not travel over the same circumferential location of the circumferential ridge 176 every time the hub 124 is reversed proximally over the male luer component 126. This led to some inconsistency in the tactile feedback the operator experiences when attempting to locate the hub 124 in a rotationally locked position with respect to the male luer component 126. To solve this problem, the splines 164a,b,c have been widened in the circumferential direction to provide narrower guideways 166. In one particular embodiment, the tubular portion 128 has a diameter of approximately 0.236 inches, the central spline 164a has a circumferential width of approximately 0.070 inches, the splines 164b have an effective circumferential width of approximately 0.035 inches, while the tapered ribs 152 are spaced apart 0.080 inches at their bases. The wider splines 164 cause the ribs 152 to travel across the same location on the circumferential ridge 176 every time the hub 124 is displaced into rotational engagement with the male luer component 126. Furthermore, the flat 176a formed on the apex of the ridge 176 reduces wear of the ridge thus further ensuring a consistent tactile feedback for the operator.

As there is no travel limiting structure in the proximal direction from the splines 164 and ridge 176, the hub 124 can be completely removed from the proximal end of the male luer component 126. As described previously, the hub 124 can be slid proximally along a supply line (not shown) to remove it from the immediate connector site.

The cam surfaces 170 on the distal end of the elongate central spline 164a ensure the proper rotational registry of the hub 124 with the splines 164. The proximal end of the ribs 152 are tapered at 178 to form guide points. As the hub 124 is slide proximally along the male luer component 126, the distal point 168 on the central spline 164a will initially contact the inwardly directed rib 152. The ribs 152 may either be aligned with the channels 166 or with the central elongate spline 164a. In the latter case, the guide points 178 will contact one or the other of the cam surfaces 170 on either side of the proximal point 168, and the hub 124 will be caused to rotate into proper rib/spline alignment. Similarly, distal travel of the hub 124 onto the male component 126 may initially bring point 172 into contact with the distal end of one of the ribs 152. Further distal advancement of the hub 124 will cause an appropriate rotational alignment of the ribs 152 into channel 166.

Alternative "Keyed" Rotational Coupling Indicator

In an alternative embodiment, a positive stop may be provided to temporarily prevent the hub 124 from being removed in a proximal direction from the male luer component 126. Referring to FIG. 12b, a central "keyed" spline 200 may be provided in place of either the spline 94a or 164a. The spline 200 is defined by a central constant width portion 202, a proximal arrowhead portion 204, and a distal arrowhead portion 206. Projections of pairs of adjacent ribs 152 are illustrated in FIG. 12b. That is, the radially inward surfaces 153 of the ribs 152 are projected on the male luer component 126. Thus, in a first position A, the ribs 152 are disposed proximate the distal arrowhead portion 206. The spacing between the ribs 152 is slightly greater than the circumferential width of the distal arrowhead portion 206. The arrowhead portion 206 is provided with an apex and a pair of adjacent cam surfaces to guide the ribs 152 therearound.

In a second position B the ribs have advanced proximally to lie adjacent the central constant width portion 202 and within the guideways 166. A proximal end of one of the ribs is prevented from further proximal movement by a stop surface 208 formed on the proximal arrowhead portion 204. Further proximal movement of the hub 124 is prevented. To remove the hub 124 from the male luer component 126, the hub is rotated, as with turning a key, to place the ribs 152 in the position C. From the position C, the hub may be translated proximally so that the ribs are in the position D, and the hub may be removed completely. In the position D, it can be seen that the proximal arrowhead portion 204 is sized slightly smaller than the spacing between the ribs 152. In the reverse sequence, the ribs are guided around the proximal arrowhead portion 204 by its taper, and then automatically around the distal arrowhead portion 206 by virtue of an angled surface 210 provided thereon. The stop surface 208 provides a positive tactile feedback indicating to the operator that the hub 124 is in an axial position in which it is rotationally locked with respect to the male luer component 126.

The embodiment shown in FIG. 12b eliminates the need for a circumferential "speed bump," but it will be appreciated that one may be provided for redundancy. For example, one or more small bumps 211 are preferably formed on the exterior of the male luer component 126 between at least two of the splines, in this case shown between the central constant width portion 202 of the spline 200 and the adjacent intermediate splines. The ribs 152 interfere with these bumps 211 so that the hub 124 must be forced thereover when rotated before being displaced proximally from the male component 126. This provides tactile feedback to the user indicating the rotational position of the hub 124.

Hub/Male Luer Component Snap Ring

In a further aspect of the present invention, a circumferential ridge or other such structure may be provided on the male luer component 126 to allow the hub 124 to be advanced distally thereon, but prevent the hub from being removed proximally. As seen in FIGS. 14a and 14b, a circumferential retaining ring 220 is illustrated projecting from the tubular portion 128 of the male luer component 126. The hub 124 advances in a distal direction as seen by the arrows 222. Diametrically opposed axial slits 224 provided in the proximal end of the male luer component 126 allow a slight inward flexing at that location when the ribs 152 cam over the retaining ring 220. In other words, the ribs 152 define a circle having approximately the same diameter as the tubular portion 128. Thus, the interference with the retaining ring 220 causes the proximal end of the male luer component 126 to be compressed inward by virtue of the slits 224. FIG. 14b illustrates the hub 124 after having been "snapped" over the retaining ring 220 and advanced distally onto the male luer component 126. The proximal end of the male luer component 126 has resiliently recovered into its original position. Reversing the direction of the hub 124 in a proximal direction over the male luer component 126 causes a rear edge 226 to come into contact with the retaining ring 220. Because there is no ramp surface on the proximal end of the ribs 152, the hub 124 is retained on the male luer component 126. In the presently illustrated form, the retaining ring 220 is rounded or angled and the hub 142 can be removed from the proximal end of the male luer component 124 with the application of sufficient force. However, other embodiments rigidly preventing removal of the hub 124 in this manner are contemplated.

Female Luer Component Protective Cap

Figures 15, 15A:
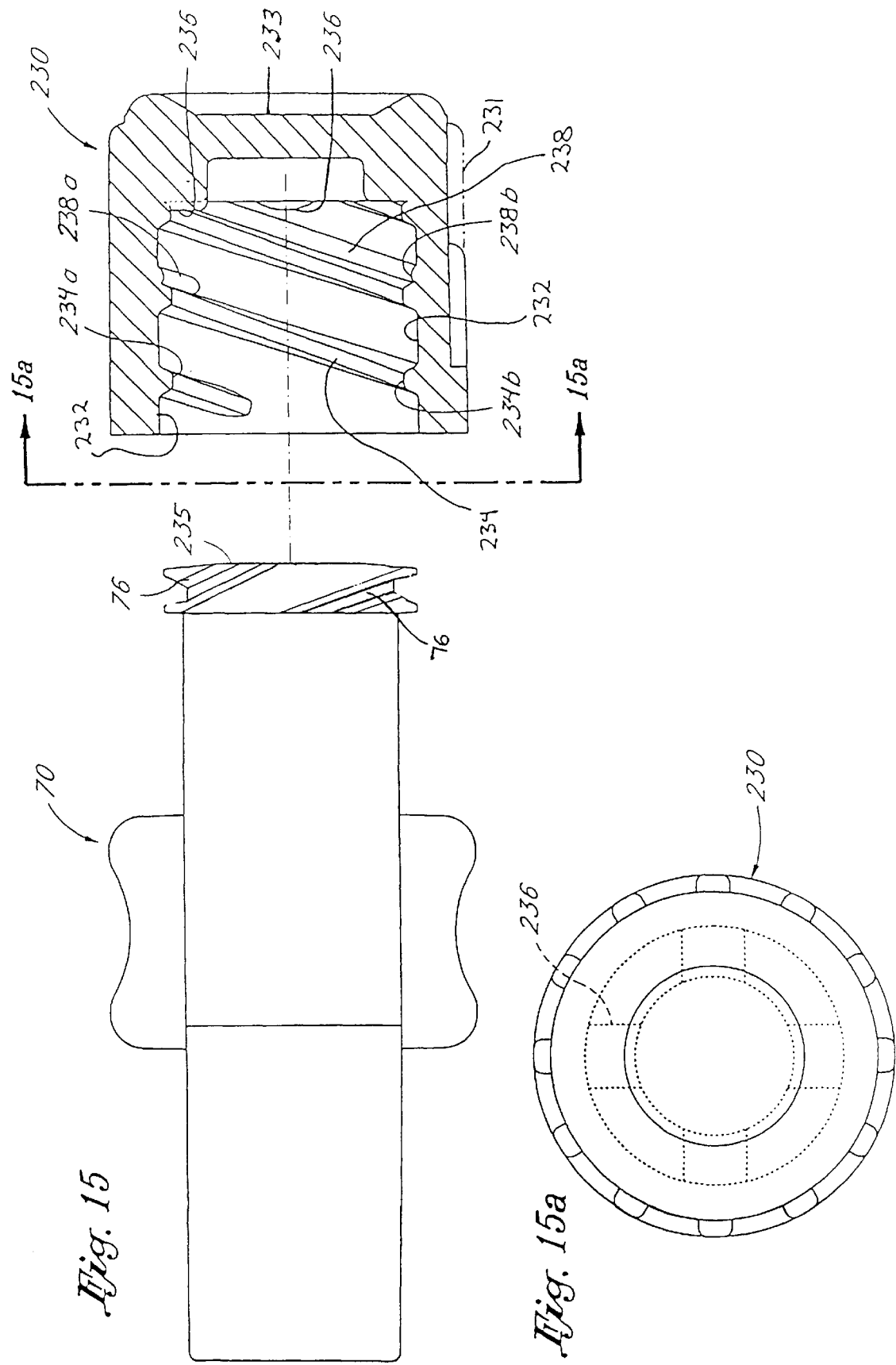
FIG. 15 is an exploded view of a female luer component and a protective cap therefore.
FIG. 15a is an elevational view of the protective cap for the female luer component taken along line 15a—15a of FIG. 15.
Figures 16, 16A:
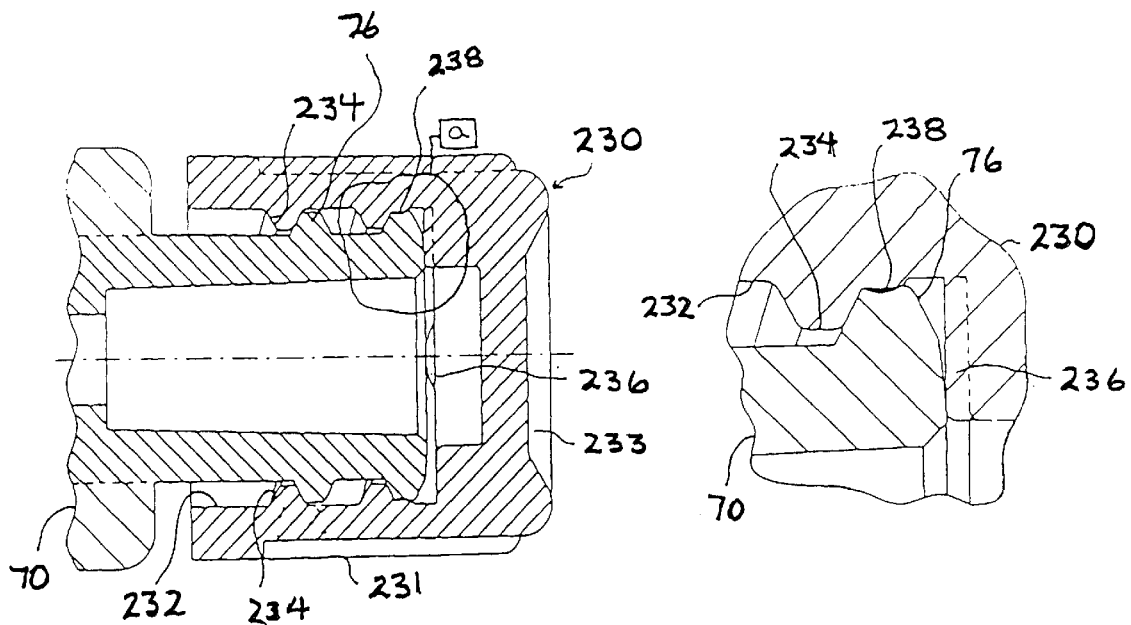
FIG. 16 is a cross-sectional view of a preferred protector cap shown engaged with a female luer component.
FIG. 16a is an exploded partial view of the frictional interference between the protective cap and the female luer component of FIG. 16.

FIGS. 15 through 16a illustrate an embodiment of a protective cap 230 for the female luer component 70 described with reference to FIGS. 1–8. As previously discussed, the female luer component 70 is provided with external threads 76. Preferably, the external threads 76 are machine threads (right hand or left hand threads) manufactured to conventional tolerances as are commonly known to those of skill in the art.

The protective cap 230 generally comprises a tubular body 231 having an inner surface 232 and a closed end or end cap 233. The protective cap 230 includes inner or internal threads 234. The internal threads 234, like the external threads 76, are preferably formed to conventional sizes and tolerances as is known to those of skill in the art. Specifically, the internal threads 234 may be configured to engage and mate with the external threads 76 within these conventional tolerances. These mating threads 76 and 234 may be any size and shape threads that allow for such engagement. Preferably, the threads 76 and 234 are conventional screw threads having conventional tolerances ranges as are known to those of skill in the art, however, the threads may be dual helical threads or other thread configurations. Preferably, the protective cap 230 includes dual threads 234a and 234b.

In use, the protective cap 230 is advanced over the female luer component 70 until a distal end 235 of the female luer component 70 contacts a plurality of radially oriented bumpers 236 provided on the interior of the closed end 233 of the cap 230. The bumpers 236 function in a similar manner as the projections 56 on the end of the protective cap 22 for the male luer component 126. In other words, the bumpers 236 provide a small gap or space between the protective cap 230 and the female luer component 70 to facilitate cleaning and sterilization while the protective cap 230 is inserted over and fully engaged with the female luer component 70. This configuration allows the female luer component 70 to vent or "breathe" with the protective cap 230 installed while providing a tortuous path to prevent contamination from entering the fluid pathway. In the alternative, the bumpers 236 may be eliminated for a non-venting or non-breather type of protective cap 230 as we describe following.

The protective cap 230 also incorporates a crush thread 238 formed on the inner surface 232. This crush thread 238 may be formed along and adjacent a portion of the interior threads 234 and protrudes radially inwardly from the inner surface 232. The crush thread 238 is configured for contacting and interfering with the external threads 76 of the female luer component 70. Preferably, the crush thread 238 comprises dual helical crush threads 238a and 238b formed along and adjacent a portion of the dual interior threads 234a and 234b. These crush threads 238a and 238b may extend radially inward such that they will contact and interfere with the major diameter of the female luer component exterior thread 76. This physical interference creates a frictional fit between the protective cap 230 and the female luer component 70 which prevents inadvertent decoupling.

The crush thread 238 may be formed adjacent a length or portion of the interior threads 234 as shown in FIG. 15a. However, the crush thread 238 may be formed in most any location within the inner surface 232 as well as being configured in a variety of configurations. For example, referring to FIGS. 16 and 16a, the crush thread 238 is formed as a rounded thread which extends radially inward and is formed within the major diameter of the last interior thread 234. In this configuration, the crush thread 238 is essentially formed between internal threads 234 such that it engages with the major diameter or outermost portion of the first external thread 76.

The crush thread 238 is preferably configured such that a relatively small surface area is exposed to a contacting external thread 76. Thus, the crush thread 238 may have a cross-sectional configuration which tapers or narrows from the inner surface 232 radially inward. Such configurations may include a triangular shape, a rounded bump shape or any other shape which minimizes the contact surface area. However, crush threads 238 having other configurations and cross-sections may also be used.

The minimized surface contact area of the crush threads 238 provides for increasing frictional interference as the protective cap 230 is further engaged with the external threads 76. When the crush thread 238 first encounters the external threads 76, it is deformed or crushed such that the surface area contacting the external threads 76 increases. As the protective cap 230 is further engaged with the external threads 76, the crush thread 238 is further deformed. The surface area of the crush thread 238 contacting the external thread 70 also increases and thus the frictional interference is increased. The crush thread 238 may be configured having different minimum diameters and cross-sectional shapes so that the amount of deformation and thus frictional interference may be adjusted accordingly.

In one embodiment, the major diameter of the female luer component threads 76 is approximately 0.306 inches, while the inner diameter of the crush threads 238a and 238b is approximately 0.300 inches, resulting in an interference of approximately 0.006 inches. This interference will yield a frictional torque resisting decoupling of the protective cap 230 of approximately 7.0 in-oz. Preferably, the interference between the crush thread 238 and the external threads 76 is between 0.001–0.009 inches and more preferably approximately 0.004–0.006 inches. However, other interference tolerances may be used and may even be preferable when using different materials and automative assembly techniques.

When using interference tolerances as previously described, the protective cap 230 advantageously resists decoupling from the luer component 70. Preferably, the resulting frictional interference is sufficient to yield a torque resisting decoupling of the protective cap 230 from the luer component 70 of between 4 to 20 in./oz. Differing frictional interferences may be used to modify or even increase the torque resisting decoupling range previously described. However, a lesser torque resisting decoupling may not sufficiently retain the protective cap 230 on the luer component 70 and a torque resisting decoupling of greater than 20 in./oz. may be impractical and unnecessary. In a preferred embodiment, the protective cap 230 is configured such that when the crush thread 238 and the external threads 76 are engaged, they have a frictional interference sufficient enough to yield a torque resisting decoupling of approximately 8 to 12 in./oz.

The crush thread 238 is preferably made from a material which is deformed when engaged with the external threads 76. This material which may be continuous with the protective cap 230 may include most any medical grade plastic. These plastics which are generally biocompatible preferably will deform under the frictional interference previously described without fracture. Thus, the crush thread 238 are preferably made from a material such as a polyethylene or a polypropolene which is slightly softer than the material forming the external thread 76 so that the crush threads 238 are actually deformed when the protective cap 230 is engaged or otherwise threaded onto the female luer component 70.

The crush threads 238a and 238b are preferably only formed on the last one-half to one turn of the internal threads 234a and 234b with sufficient length to run past the major diameter of the female external thread 76 to prevent compression and a possible set from occurring during sterilization. In addition, by leaving the crush threads 238 and 238b to the last one-half to one threaded turn, assembly of the protective cap 230 on the luer component 70 is simplified. The crush threads 238a and 238b are desirably disposed approximately 180 degrees apart to prevent "cocking" of the protecting cap 230 when threaded over the female luer component 70. Previous attempts at creating an interference between a protective cap and a female component consisted of forming the internal threads with a smaller minor diameter. Since the protective cap 230 is often hard to assemble on the end of the female luer component 70 due to its tolerance extremes, fatigue of the assembler may result. The protective cap of the present invention allows the internal threads 234a and 234b on the protective cap 230 to be sized to fit easily over the female luer component 70 even after shrinkage, and the crush threads 238a and 238b provide an interference during the latter part of the assembly.

Figures 17, 17A:
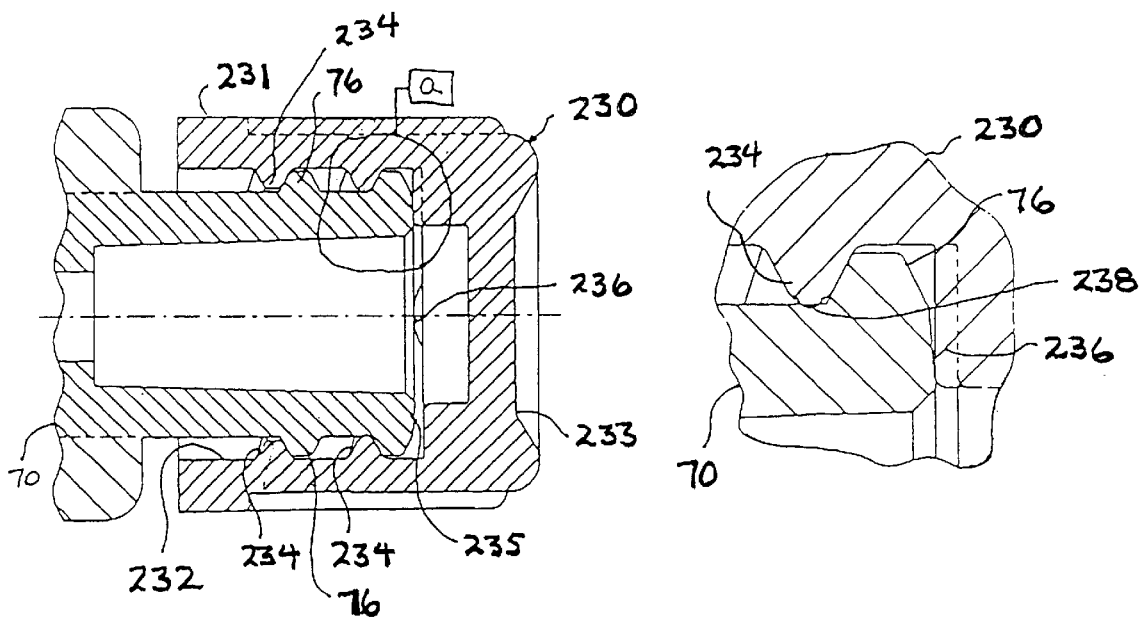
FIG. 17 is a cross-sectional view of an alternative embodiment of a preferred protector cap engaged with a female luer component.
FIG. 17a is an exploded partial view of the frictional interference between the protective cap and the female luer component of FIG. 17.

Other variations and configurations of crush threads 238 are contemplated. For example, FIGS. 17 and 17a show a crush thread formed on the top or minor diameter of the internal thread 234. In this configuration, the crush thread 238 contacts the minor diameter of the external threads 76. In yet another configuration, the crush threads 238 are configured along the tapering side of the internal thread 234 such that it contacts the tapering side of the mating external thread 76. Other variations include altering the dimensions of the crush threads 238a and 238b such that they have a varying pitch toward the closed end 233 of the protective cap 230. Alternatively, the crush threads 238a and 238b may be formed having a first pitch and wherein the external threads 76 have a second pitch. By providing a varying the first pitch from the second pitch, frictional interference is created. The crush threads 238 may also be replaced with discrete bumps or other protrusions which extend radially inwardly from the inner surface 232 and interfere with the external thread 76. Preferably, these protrusions are formed adjacent a portion of the inner threads 234 for direct contact and interference with the external threads 76.

Figures 18, 18A:
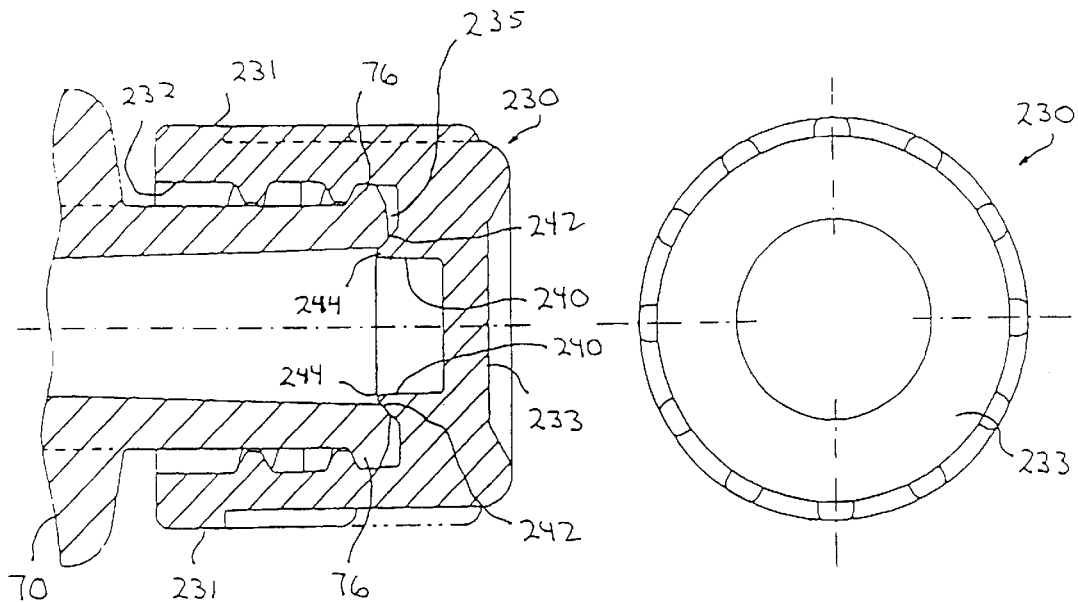
Figure 19:
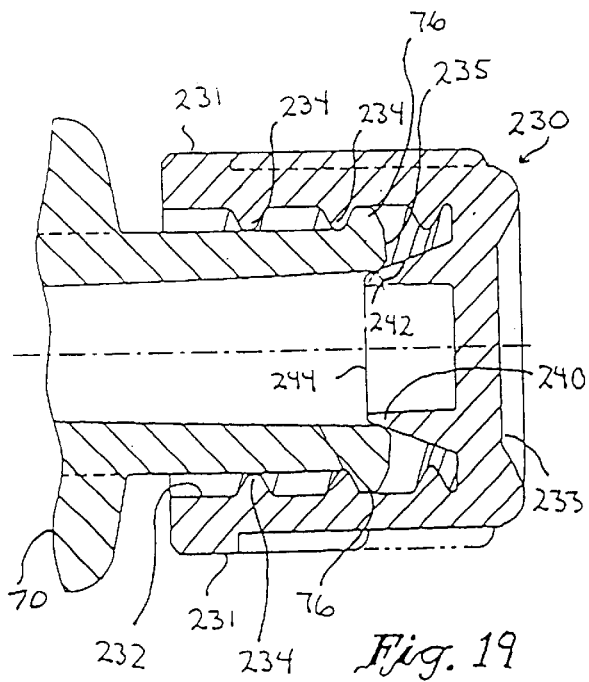
FIG. 19 is a cross-sectional view of an alternative embodiment of a preferred protector cap having a sealing ring and shown engaged with a female luer component.

In an alternative configuration, the protective cap 230 may be configured as a sealed or non-breather type cap. In this embodiment, as shown in FIGS. 18–19, the distal end 235 of the female luer component 70 may form a seal with the interior of the closed end 233 of the protective cap 230. Preferably, a sealing ring 240 is mounted on the interior of the closed end 233 for contacting and sealing against the distal end 235. The sealing ring 240 may have a protruding or tapering portion 242 which extends axially outward from the interior of the closed end 233 to engage and seal against the proximal end of the luer component 70. The tapered portion 242 may be configured having a distal end 244 which may fit within and contact against the inner surface of the open lumen 78 when the protective cap 230 is connected.

The sealing ring 240 may be made from a deformable material similar to that used for the crush threads 238 or alternatively may be made from a less or non-deformable material. Preferably the protective cap 230, including the crush threads 238 and the sealing ring 240, may be made from a single molded piece. As previously described, the crush thread 238 is preferably located on the inner surface 232 such that the protective cap 230 is within one-half to one turn prior to the sealing ring 240 engaging and sealing with the luer component 70.

When using a sealing ring 240 made from a material that is softer than the luer component 70 or an otherwise deformable material, engagement with the distal end 235 may crush, compress, or otherwise deform the sealing ring 240. This deformation creates a frictional interference which resists decoupling. Thus, when using a sealing ring 240, the crush thread 238 may be omitted. However, the crush thread 238 may preferably be retained to ensure decoupling will not occur.

The amount of deformation and thus frictional interference may be controlled by varying the angle of the tapered portion 242. Preferably, this angle is between 5 and 45 degrees as measured from a parallel to the radial axis of the protective cap 230. With this orientation, a taper of 45 degrees would be a blunt or flat interior surface of the closed end 233. An alternative sealing ring, such as a O-ring or other similar sealing component to be inserted between the proximal end of the luer component 70 and the inner surface 232 of the closed end 233 to provide a seal.

One-Piece Hub/Male Luer Component

FIG. 20 illustrates a one-piece hub/male luer component 250. In this embodiment, a hub portion 252 is formed integrally with a male luer portion 254. Although some versatility is lost because the hub portion 252 no longer spins freely with respect to the male luer portion 254, the one-piece component 250 is often desirable. In particular, in small tubing (conduit) applications. The one-piece component 250 facilitates axial engagement of the tapered nose 256 with the inner taper on a female luer component. If desired, the inner threads on the hub portion 252 can engage the threads on the female luer component to lock the connector together.

Hex Anti-Rotation Coupling

Another type of anti-rotation structure between a male luer component 260 and an outer hub 262 is seen in FIGS. 21 and 22. The male component 260 comprises a distal nose portion 264, a proximal hose-receiving tube 26, and a cylindrical flange 268 therebetween. An inner lumen is defined by three passages increasing in size from the distal end to proximal end. More particularly, the lumen includes a distal first passage 270a, and a second passage 270b, and a third passage 270c. Two transition regions 272a, 272b provided hose stops between the first and second passages 270a,b and between the second and third passages 270c,c, respectively.

The hub 262 has a generally cylindrical sleeve portion 274 with a circular lip 276 extending radially inward at a proximal end. The lip 276 includes a polygonal inner edge 278, preferably formed as a dodecahedron with 12 sides, which mates with a polygonal exterior portion 280, preferably formed as a hexagon, on the male component 260 adjacent to the flange 268 in the proximal direction. The polygonal inner edge 278 includes parallel sides spaced apart a distance less than the outer diameter of the flange 268. Thus, the hub 262 is prevented from axial travel along the male component 260 by virtue of the interference between the inner edge 278 and flange 268. The hub 262 can thus be used to axially displace the male component 260 into engagement with a female component (not shown) to form a luer connection. To assist in engaging or disengaging the luer connection, the hub 262 rotationally couples with the male component 260 at the polygonal inner edge 278 and polygonal exterior portion 280. Thus, tight fits between the nose portion 264 and tapered lumen of the female component may be broken more easily by rotating the hub 262 with respect to the wings of the female component.

Ratchet-Type Hub/Male Component Coupling

FIGS. 23 and 24 illustrate a coupling between a hub 290 and a male luer component 292 which prevents relative rotation in one direction yet allows limited relative rotation in the other direction. More specifically, the hub 290 may advance the male luer component 292 onto a female luer component, whereupon the hub can rotate freely relative to the male component without causing the male luer to twist.

The male component 292 comprises a tubular hose-receiving portion 294 having exterior ratchet splines 296 thereon, a tapered shoulder 298 and a distal nose 300. A central stepped lumen 302 extends through the male component 292. The hub 290 is defined by a sleeve-like portion 304 having internal threads 306, a proximal region 308 having a plurality of cantilevered fingers 310 separated by axial gaps 312, and a transition region 313 with an internal taper 314. The fingers 310 are distributed around and extend proximally from the transition region 313 to form a plurality of curved cantilevered beams surrounding the tubular portion 294 of the male component 292.

As seen in FIG. 24, the inner surface of each finger 310 defines at least two and preferably three axially aligned teeth 316 sized and shaped to mate with the splines 296. The teeth 316 and splines are so configured to allow the fingers 310 to cam over the splines when the hub 290 rotates with respect to the male component 292 in a clockwise direction as viewed from the perspective of FIG. 24. This rotation corresponds to the direction for advancing the threads 306 onto the female component. The resiliency of the fingers 310 is great enough to withstand relative hub/male component rotation, however, below a certain relative torque threshold.

The male component 292 is rotated along with the hub 292 as the hub advances on the female component by virtue of the interference between the tapered shoulder 298 and internal taper 314 until the nose 300 is firmly lodged in a tapered lumen. At this point, the hub 290 "skips" over the male component and the teeth 316 make an audible clidking sound as they cam over the splines 296. In this manner, twisting of the luer connection is prevented during assembly of a male component to a female component. Overtightening is prevented by the interference between the 45° of the tapered shoulder 298 and internal taper 314. Reverse rotation of the hub 290 with respect to the male component 292 is prevented by the specific shape of the spline/teeth interface, so that the luer connection remains secure despite vibration or inadvertent jostling. The luer connection is broken by forced rotation of the hub 290 in a counter-clockwise direction while holding firm the female component wings.

Although the present invention has been described in terms of certain preferred embodiments, other embodiments can be readily devised by one of skill in the art in view of the foregoing, which will also use the basic concepts of the present invention. Accordingly, the scope of the present invention is to be defined by reference to the attached claims.

What is claimed is:

1. An intravenous system for the introduction of an intravenous fluid into a vein of a patient, comprising:

a source of the intravenous fluid;

a flow-through conduit extending between the source of the intravenous fluid and the vein of the patient, the conduit providing communication between the source and the patient to facilitate introduction of the intravenous fluid from the source into the vein of the patient;

a medical luer component disposed along the conduit between the source and the patient, the component having an elongate tubular body and an end with external threads;

a protective cap sized and configured to fit over the end of the medical luer component;

a tubular body included in the protective cap, the body having an inner surface and a closed end;

internal threads included in the protective cap and being disposed on the inner surface of the body, said internal threads being sized and shaped to engage the external thread on said medical luer component for coupling said protective cap with said medical luer component to form a medical luer connection;

a crush thread included in the protective cap and being formed adjacent said internal threads, the crush thread protruding radially inwardly for contacting and interfering with said external threads on said medical luer component; and the crushed thread having properties for being crushed upon itself by the external thread of the medical luer component to increase the torsional resistance decoupling of the protective cap from the medical luer component.

2. The intravenous system recited in claim 1 wherein said crush thread is formed between a pair of adjacent threads within a major diameter of said tubular body.

3. The intravenous system recited in claim 1 wherein said crush thread is formed on top of a portion of said inner threads along a minor diameter of said body.

4. The intravenous system recited in claim 1 wherein said crush thread is made from a material which is softer than said external threads on said medical luer component such that said crush thread is deformed when mated with said external threads.

5. The intravenous system recited in claim 1 wherein said cap is made from a medical grade plastic.

6. The intravenous system recited in claim 1 wherein said medical grade plastic is a polyethylene.

7. The intravenous system recited in claim 1 wherein said medical grade plastic is a polypropylene.

8. The intravenous system recited in claim 1 and further comprising a protrusion extending inwardly from said closed end for contact with said proximal end of said medical luer component to provide a small gap adjacent to protrusion between the protective cap and said medical luer component.

9. The intravenous system recited in claim 1 wherein said crush thread is a dual helical thread.

10. The intravenous system recited in claim 1 wherein said crush thread extends radially inwardly to define an internal minor diameter which is sufficiently smaller than a major diameter of said external threads of said medical luer component to cause a frictional interference when engaged, and wherein said interference causes at least a portion of said crush thread to deform.

11. The protective cap as recited in claim 10 wherein said distal end of said crush thread is deformable when engaged with said external threads of said medical luer component to form an increased surface area in contact with said external threads and wherein said increased surface area increases the frictional interference between the protective cap and the medical luer component.

12. The intravenous system recited in claim 10 wherein the crush thread of the cap and the external threads of the medical luer component, when engaged, have a frictional interference sufficient to yield a torsional resistance to decoupling of the protective cap from the medical luer component of approximately between 4 and 20 inch-ounces.

13. The intravenous system recited in claim 12, wherein the crush thread and said external threads of said medical luer component, when engaged, have a frictional interference sufficient to yield a torsional resistance to decoupling of between 8 and 12 inch-ounces.

14. The intravenous system recited in claim 10 and further comprising a sealing ring extending axially inwardly from said protective cap the sealing ring having properties for contacting and sealing against the proximal end of said medical luer connector.

15. The intravenous system recited in claim 14 wherein said sealing ring is disposed axially between the crush threads and the closed end of the body.

16. A intravenous system as recited in claim 10 wherein said crush thread has a first pitch and said external threads have a second pitch.

17. A intravenous system recited in claim 10 wherein said internal threads comprises dual internal threads.

18. The intravenous system recited in claim 1, wherein the crush thread is a first crush thread and the medical luer connection further comprises:

a second crush thread forming a dual helical crush thread with the first crush thread.

19. The intravenous system recited in claim 1, wherein the crush thread is formed along less than the entire length of the internal thread of the protective cap.

20. The intravenous system recited in claim 19, wherein:

the internal thread has multiple revolutions including a last revolution; and the crush thread is formed totally within the last revolution of the internal thread.

21. The intravenous system recited in claim 1 wherein:

the crush thread in radial cross-section extends inwardly from a maximum diameter at the inner surface to a minimum diameter; and the minimum diameter is variable along the length of the crush thread.

22. The intravenous system recited in claim 1, wherein the crush thread in radial cross-section has a shape that varies along the length of the crush thread.

23. The medical luer connection recited in claim 1, wherein the crush thread of the protective cap and the external thread of the medical luer component have an interference fit in a range between 0.001 and 0.009 inches.

24. The intravenous system recited in claim 23, wherein the interference fit is in a range between 0.004 and 0.006 inches.

* * * * *